US009109256B2

(12) United States Patent
Shuber

(10) Patent No.: US 9,109,256 B2
(45) Date of Patent: Aug. 18, 2015

(54) METHOD FOR MONITORING DISEASE PROGRESSION OR RECURRENCE

(75) Inventor: Anthony P. Shuber, Mendon, MA (US)

(73) Assignee: Esoterix Genetic Laboratories, LLC, Burlington, NC (US)

( * ) Notice: Subject to any disclaimer, the term of this patent is extended or adjusted under 35 U.S.C. 154(b) by 250 days.

(21) Appl. No.: 11/666,561

(22) PCT Filed: Oct. 27, 2005

(86) PCT No.: PCT/US2005/039670
§ 371 (c)(1),
(2), (4) Date: Feb. 4, 2008

(87) PCT Pub. No.: WO2006/047787
PCT Pub. Date: May 4, 2006

(65) Prior Publication Data
US 2008/0161420 A1    Jul. 3, 2008

Related U.S. Application Data

(60) Provisional application No. 60/623,005, filed on Oct. 27, 2004, provisional application No. 60/627,248, filed on Nov. 12, 2004.

(51) Int. Cl.
*C12Q 1/68* (2006.01)
(52) U.S. Cl.
CPC ........ *C12Q 1/6886* (2013.01); *C12Q 2600/118* (2013.01); *C12Q 2600/154* (2013.01); *Y10T 436/145555* (2015.01)

(58) Field of Classification Search
None
See application file for complete search history.

(56) References Cited

U.S. PATENT DOCUMENTS

| | | |
|---|---|---|
| 4,072,574 A | 2/1978 | Loeb et al. |
| 4,101,279 A | 7/1978 | Aslam |
| 4,309,782 A | 1/1982 | Paulin |
| 4,333,734 A | 6/1982 | Fleisher |
| 4,445,235 A | 5/1984 | Slover et al. |
| 4,535,058 A | 8/1985 | Weinberg et al. |
| 4,705,050 A | 11/1987 | Markham |
| 4,786,718 A | 11/1988 | Weinberg et al. |
| 4,857,300 A | 8/1989 | Maksem |
| 4,863,849 A | 9/1989 | Melamede |
| 4,871,838 A | 10/1989 | Bos et al. |
| 4,968,602 A | 11/1990 | Dattagupta |
| 4,968,603 A | 11/1990 | Slamon et al. |
| 4,988,617 A | 1/1991 | Landegren et al. |
| 5,075,217 A | 12/1991 | Weber |
| 5,087,617 A | 2/1992 | Smith |
| 5,126,239 A | 6/1992 | Livak et al. |
| 5,137,806 A | 8/1992 | LeMaistre et al. |
| 5,141,849 A | 8/1992 | Chou |
| 5,149,506 A | 9/1992 | Skiba et al. |
| 5,185,244 A | 2/1993 | Wallace |
| 5,196,167 A | 3/1993 | Guadagno et al. |
| 5,202,231 A | 4/1993 | Drmanac et al. |
| 5,248,671 A | 9/1993 | Smith |
| 5,272,057 A | 12/1993 | Smulson et al. |
| 5,296,349 A | 3/1994 | Wallace |
| 5,302,509 A | 4/1994 | Cheeseman |
| 5,330,892 A | 7/1994 | Vogelstein et al. |
| 5,331,973 A | 7/1994 | Fiedler et al. |
| 5,348,855 A | 9/1994 | Dattagupta et al. |
| 5,352,775 A | 10/1994 | Albertsen et al. |
| 5,362,623 A | 11/1994 | Vogelstein et al. |
| 5,369,004 A | 11/1994 | Polymeropoulos et al. |
| 5,378,602 A | 1/1995 | Polymeropoulos et al. |
| 5,380,645 A | 1/1995 | Vogelstein |
| 5,380,647 A | 1/1995 | Bahar |
| 5,382,510 A | 1/1995 | Levine et al. |
| 5,409,586 A | 4/1995 | Kamahori et al. |
| 5,455,166 A | 10/1995 | Walker |
| 5,458,761 A | 10/1995 | Kamahori et al. |
| 5,463,782 A | 11/1995 | Carlson et al. |
| 5,466,576 A | 11/1995 | Schulz et al. |
| 5,468,610 A | 11/1995 | Polymeropoulos et al. |
| 5,468,613 A | 11/1995 | Erlich et al. |
| 5,489,508 A | 2/1996 | West et al. |
| 5,492,808 A | 2/1996 | de la Chapelle et al. |
| 5,496,470 A | 3/1996 | Lenhart |
| 5,496,699 A | 3/1996 | Sorenson |
| 5,508,164 A | 4/1996 | Kausch et al. |
| 5,512,441 A | 4/1996 | Ronai |
| 5,514,547 A | 5/1996 | Balazs et al. |
| 5,527,676 A | 6/1996 | Vogelstein et al. |
| 5,532,108 A | 7/1996 | Vogelstein |
| 5,545,527 A | 8/1996 | Stevens et al. |
| 5,552,283 A | 9/1996 | Diamandis et al. |

(Continued)

FOREIGN PATENT DOCUMENTS

| | | |
|---|---|---|
| AU | A-11325/95 | 4/1996 |
| EP | 0 063 879 A2 | 11/1982 |

(Continued)

OTHER PUBLICATIONS

Syvanen, "Solid-phase minisequencing" in Laboratory Methods for the Detection of Mutations and Polymorphisms in DNA, 1997, Taylor (ed.), CRC Press, Boca Raton, pp. 53-64.*
Wong et al, in Microarrays and Cancer Research, 2002, Warrington et al (eds.), Eaton Publishing, Westboro, MA, pp. 129-138.*
Alizadeh et al, Nature 403: 503 (2000).*
Strausberg et al, in Microarrays and Cancer Research, 2002, Warrington et al (eds.), Eaton Publishing, Westborough, MA, pp. xi-xvi.*
Notterman et al, in Microarrays and Cancer Research, 2002, Warrington et al (eds.), Eaton Publishing, Westborough, MA, pp. 81-111.*

(Continued)

*Primary Examiner* — James Martinell
(74) *Attorney, Agent, or Firm* — Kilpatrick Townsend & Stockton LLP

(57) ABSTRACT

The invention provides methods for detecting and monitoring diseases associated with genetic abnormalities in a subject.

39 Claims, No Drawings

(56) References Cited

U.S. PATENT DOCUMENTS

| | | |
|---|---|---|
| 5,561,041 A | 10/1996 | Sidransky |
| 5,569,584 A | 10/1996 | Augenlicht |
| 5,571,676 A | 11/1996 | Shuber |
| 5,578,458 A | 11/1996 | Caskey et al. |
| 5,589,330 A | 12/1996 | Shuber |
| 5,589,335 A | 12/1996 | Kearney et al. |
| 5,604,099 A | 2/1997 | Erlich et al. |
| 5,610,287 A | 3/1997 | Nikiforov et al. |
| 5,616,463 A | 4/1997 | Fornace, Jr. et al. |
| 5,627,032 A | 5/1997 | Ulanovsky |
| 5,633,134 A | 5/1997 | Shuber |
| 5,635,347 A | 6/1997 | Link et al. |
| 5,635,352 A | 6/1997 | Urdea et al. |
| 5,645,995 A | 7/1997 | Kieback |
| 5,648,212 A | 7/1997 | Albertsen et al. |
| 5,650,277 A | 7/1997 | Navot et al. |
| 5,650,281 A | 7/1997 | Vogelstein |
| 5,670,325 A | 9/1997 | Lapidus et al. |
| 5,683,877 A | 11/1997 | Lu-Chang et al. |
| 5,687,716 A | 11/1997 | Kaufmann et al. |
| 5,709,998 A | 1/1998 | Kinzler et al. |
| 5,710,028 A | 1/1998 | Eyal et al. |
| 5,726,019 A | 3/1998 | Sidransky |
| 5,741,650 A | 4/1998 | Lapidus et al. |
| 5,753,439 A | 5/1998 | Smith et al. |
| 5,759,777 A | 6/1998 | Kearney et al. |
| 5,798,266 A | 8/1998 | Quay et al. |
| 5,830,665 A | 11/1998 | Shuber et al. |
| 5,834,181 A | 11/1998 | Shuber |
| 5,834,193 A | 11/1998 | Kozlowski et al. |
| 5,846,710 A | 12/1998 | Bajaj |
| 5,856,092 A | 1/1999 | Dale et al. |
| 5,866,323 A | 2/1999 | Markowitz et al. |
| 5,885,775 A | 3/1999 | Haff et al. |
| 5,888,778 A | 3/1999 | Shuber |
| 5,888,819 A | 3/1999 | Goelet et al. |
| 5,910,407 A | 6/1999 | Vogelstein et al. |
| 5,928,870 A | 7/1999 | Lapidus et al. |
| 5,945,284 A | 8/1999 | Livak et al. |
| 5,952,178 A | 9/1999 | Lapidus et al. |
| 5,958,684 A | 9/1999 | Van Leeuwen et al. |
| 5,976,798 A | 11/1999 | Parker et al. |
| 5,976,842 A | 11/1999 | Wurst |
| 5,981,180 A | 11/1999 | Chandler et al. |
| 6,013,431 A | 1/2000 | Soderlund et al. |
| 6,017,704 A | 1/2000 | Herman et al. |
| 6,020,124 A | 2/2000 | Sorenson |
| 6,020,137 A | 2/2000 | Lapidus et al. |
| 6,084,091 A | 7/2000 | Muller et al. |
| 6,100,029 A | 8/2000 | Lapidus et al. |
| 6,100,040 A | 8/2000 | Ramberg |
| 6,107,032 A | 8/2000 | Kilger et al. |
| 6,107,061 A | 8/2000 | Johnson |
| 6,110,678 A | 8/2000 | Weisburg et al. |
| 6,114,114 A | 9/2000 | Seilhamer et al. |
| 6,130,049 A | 10/2000 | Paul et al. |
| 6,143,529 A | 11/2000 | Lapidus et al. |
| 6,146,828 A | 11/2000 | Lapidus et al. |
| 6,150,117 A | 11/2000 | Zetter et al. |
| 6,153,379 A | 11/2000 | Caskey et al. |
| 6,177,251 B1 | 1/2001 | Vogelstein et al. |
| 6,180,408 B1 | 1/2001 | Kwok et al. |
| 6,203,993 B1 | 3/2001 | Shuber et al. |
| 6,214,558 B1 | 4/2001 | Shuber et al. |
| 6,221,592 B1 | 4/2001 | Schwartz et al. |
| 6,225,092 B1 | 5/2001 | Kilger et al. |
| 6,228,596 B1 | 5/2001 | Macina et al. |
| 6,235,486 B1 * | 5/2001 | Young et al. ............... 435/7.1 |
| 6,251,638 B1 | 6/2001 | Umansky et al. |
| 6,258,540 B1 | 7/2001 | Lo et al. |
| 6,265,229 B1 | 7/2001 | Fodstad et al. |
| 6,268,136 B1 | 7/2001 | Shuber et al. |
| 6,280,947 B1 | 8/2001 | Shuber et al. |
| 6,300,077 B1 | 10/2001 | Shuber et al. |
| 6,303,304 B1 | 10/2001 | Shuber et al. |
| 6,312,893 B1 | 11/2001 | Van Ness et al. |
| 6,351,857 B2 | 3/2002 | Slaon, III et al. |
| 6,355,433 B1 | 3/2002 | Xu et al. |
| 6,361,940 B1 | 3/2002 | Van Ness et al. |
| 6,406,857 B1 | 6/2002 | Shuber et al. |
| 6,415,555 B1 | 7/2002 | Montague |
| 6,428,964 B1 | 8/2002 | Shuber |
| 6,458,544 B1 | 10/2002 | Miller |
| 6,475,738 B2 | 11/2002 | Shuber et al. |
| 6,482,595 B2 | 11/2002 | Shuber et al. |
| 6,498,012 B2 | 12/2002 | Laken |
| 6,503,718 B2 | 1/2003 | Shuber et al. |
| 6,518,026 B2 | 2/2003 | Hartley |
| 6,534,273 B2 | 3/2003 | Weisburg et al. |
| 6,551,777 B1 | 4/2003 | Shuber et al. |
| 6,566,101 B1 | 5/2003 | Shuber et al. |
| 6,586,177 B1 | 7/2003 | Shuber |
| 6,605,433 B1 * | 8/2003 | Fliss et al. .................. 435/6 |
| 6,818,404 B2 | 11/2004 | Shuber |
| 6,844,155 B2 | 1/2005 | Shuber |
| 6,919,174 B1 | 7/2005 | Shuber |
| 7,432,050 B2 | 10/2008 | Markowitz |
| 7,485,420 B2 | 2/2009 | Markowitz |
| 2001/0018180 A1 | 8/2001 | Shuber et al. |
| 2001/0039012 A1 | 11/2001 | Lapidus |
| 2001/0042264 A1 | 11/2001 | Sloan et al. |
| 2002/0001800 A1 | 1/2002 | Lapidus |
| 2002/0004201 A1 | 1/2002 | Lapidus et al. |
| 2002/0009727 A1 | 1/2002 | Schultz et al. |
| 2002/0012922 A1 | 1/2002 | Hilbush et al. |
| 2002/0025525 A1 | 2/2002 | Shuber |
| 2002/0040498 A1 | 4/2002 | Sloan et al. |
| 2002/0045183 A1 | 4/2002 | Shuber et al. |
| 2002/0048752 A1 | 4/2002 | Lapidus et al. |
| 2002/0064787 A1 | 5/2002 | Shuber et al. |
| 2002/0102604 A1 | 8/2002 | Milne Edwards et al. |
| 2002/0110810 A1 | 8/2002 | Shuber |
| 2002/0119469 A1 | 8/2002 | Shuber et al. |
| 2002/0119472 A1 | 8/2002 | Lapidus et al. |
| 2002/0123052 A1 | 9/2002 | Laken |
| 2002/0132251 A1 | 9/2002 | Shuber |
| 2002/0164631 A1 | 11/2002 | Shuber et al. |
| 2003/0044780 A1 | 3/2003 | Lapidus et al. |
| 2003/0049659 A1 | 3/2003 | Lapidus et al. |
| 2003/0064385 A1 * | 4/2003 | Dressman et al. ............ 435/6 |
| 2003/0087258 A1 | 5/2003 | Shuber |
| 2003/0138793 A1 * | 7/2003 | Su et al. .................... 435/6 |
| 2005/0247563 A1 | 11/2005 | Shuber et al. |
| 2008/0145852 A1 | 6/2008 | Shuber |

FOREIGN PATENT DOCUMENTS

| | | |
|---|---|---|
| EP | 0 185 494 A2 | 6/1986 |
| EP | 0 259 031 B1 | 3/1988 |
| EP | 0 284 362 A2 | 9/1988 |
| EP | 0 332 435 A2 | 9/1989 |
| EP | 0 332 435 B1 | 9/1989 |
| EP | 0 337 498 A2 | 10/1989 |
| EP | 0 063 879 B1 | 11/1989 |
| EP | 0 390 323 A2 | 10/1990 |
| EP | 0 390 323 A3 | 10/1990 |
| EP | 0 407 789 A1 | 1/1991 |
| EP | 0 407 789 B1 | 1/1991 |
| EP | 0 408 918 A1 | 1/1991 |
| EP | 0 408 918 B1 | 1/1991 |
| EP | 0 497 527 A1 | 8/1992 |
| EP | 0 608 004 A2 | 7/1994 |
| EP | 0 664 339 A1 | 7/1995 |
| EP | 1 251 183 A2 | 10/2002 |
| GB | 2 293 238 A | 3/1996 |
| WO | WO-89/11211 | 11/1989 |
| WO | WO-90/09455 | 8/1990 |
| WO | WO-91/02087 | 2/1991 |
| WO | WO-91/13075 | 9/1991 |
| WO | WO-92/13103 | 8/1992 |
| WO | WO-92/15712 | 9/1992 |
| WO | WO-92/16657 | 10/1992 |
| WO | WO-93/06240 | 4/1993 |
| WO | WO-93/18186 | 9/1993 |

(56) References Cited

FOREIGN PATENT DOCUMENTS

| | | |
|---|---|---|
| WO | WO-93/20233 | 10/1993 |
| WO | WO-93/20235 | 10/1993 |
| WO | WO-93/25563 | 12/1993 |
| WO | WO-94/00603 | 1/1994 |
| WO | WO-94/01447 | 1/1994 |
| WO | WO-94/09161 | 4/1994 |
| WO | WO-94/10575 | 5/1994 |
| WO | WO-94/11383 | 5/1994 |
| WO | WO-94/23055 | 10/1994 |
| WO | WO-95/00669 | 1/1995 |
| WO | WO-95/07361 | 3/1995 |
| WO | WO-95/09928 | 4/1995 |
| WO | WO-95/09929 | 4/1995 |
| WO | WO-95/12606 | 5/1995 |
| WO | WO-95/12607 | 5/1995 |
| WO | WO-95/13397 | 5/1995 |
| WO | WO-95/14108 | 5/1995 |
| WO | WO-95/15400 | 6/1995 |
| WO | WO-95/16792 | 6/1995 |
| WO | WO-95/18818 | 7/1995 |
| WO | WO-95/19448 | 7/1995 |
| WO | WO-95/20680 | 8/1995 |
| WO | WO-95/25813 | 9/1995 |
| WO | WO-95/31728 | 11/1995 |
| WO | WO-96/01907 | 1/1996 |
| WO | WO-96/02671 | 2/1996 |
| WO | WO-96/06951 | 3/1996 |
| WO | WO-96/08514 | 3/1996 |
| WO | WO-96/12821 | 5/1996 |
| WO | WO-96/13611 | 5/1996 |
| WO | WO-96/23895 A | 8/1996 |
| WO | WO-96/30545 | 10/1996 |
| WO | WO-97/09449 | 3/1997 |
| WO | WO-97/09600 | 3/1997 |
| WO | WO-97/22719 | 6/1997 |
| WO | WO-97/23651 | 7/1997 |
| WO | WO-97/25442 | 7/1997 |
| WO | WO-97/28450 | 8/1997 |
| WO | WO-98/13522 | 4/1998 |
| WO | WO-98/14616 | 4/1998 |
| WO | WO-98/38338 | 9/1998 |
| WO | WO-98/39474 | 9/1998 |
| WO | WO-98/39478 | 9/1998 |
| WO | WO-98/58081 | 12/1998 |
| WO | WO-98/58084 | 12/1998 |
| WO | WO-99/20798 | 4/1999 |
| WO | WO-99/28507 | 6/1999 |
| WO | WO-99/43851 | 9/1999 |
| WO | WO-99/45147 | 9/1999 |
| WO | WO-99/53316 | 10/1999 |
| WO | WO-99/55912 | 11/1999 |
| WO | WO-99/60160 | 11/1999 |
| WO | WO-99/60161 | 11/1999 |
| WO | WO-99/60162 | 11/1999 |
| WO | WO-99/66077 | 12/1999 |
| WO | WO-00/09751 | 2/2000 |
| WO | WO-00/11215 | 3/2000 |
| WO | WO-00/31298 | 6/2000 |
| WO | WO-00/31303 | 6/2000 |
| WO | WO-00/31305 | 6/2000 |
| WO | WO-00/32820 | 6/2000 |
| WO | WO-00/42223 | 7/2000 |
| WO | WO-00/50640 | 8/2000 |
| WO | WO-00/58514 | 10/2000 |
| WO | WO-00/61808 | 10/2000 |
| WO | WO-00/66005 | 11/2000 |
| WO | WO-00/70096 | 11/2000 |
| WO | WO-01/11083 | 2/2001 |
| WO | WO-01/18252 | 3/2001 |
| WO | WO-01/42502 | 6/2001 |
| WO | WO-01/42503 | 6/2001 |
| WO | WO-01/42781 | 6/2001 |
| WO | WO-01/64950 A2 | 9/2001 |
| WO | WO-02/055740 | 7/2002 |
| WO | WO-02/059379 | 8/2002 |
| WO | WO-02/074995 | 9/2002 |
| WO | WO-02/092858 | 11/2002 |
| WO | WO-02/099126 | 12/2002 |
| WO | WO-03/044217 | 5/2003 |
| WO | WO-03/071252 | 8/2003 |
| WO | WO 03/071252 A3 | 8/2003 |
| WO | WO-03/104427 A | 12/2003 |
| WO | WO-2004/007773 | 1/2004 |
| WO | WO-2004/113574 A | 12/2004 |
| WO | WO 2005/017207 A2 | 2/2005 |
| WO | WO-2005/111244 A3 | 11/2005 |
| WO | WO-2007/044071 A3 | 4/2007 |

OTHER PUBLICATIONS

Ma et al, Oncogene 19: 2739 (2000).*
Aaltonen et al (1994) "Replication Errors in Benign and Malignant Tumors from Hereditary Nonpolyposis Colorectal Cancer Patients" Cancer Research 54:1645-1648.
Aaltonen et al (1998) "Incidence of Hereditary Nonpolyposis Colorectal Cancer and the Feasibility of Molecular Screening for the Disease" The New England Journal of Medicine 338:1481-1487.
Abarzua et al (1984) "Enzymatic techniques for the isolation of random single-base substitutions in vitro at high frequency" Proc. Natl. Acad. Sci., 81:2030-2034.
Agathanggelou et al. (2001) "Methylation associated inactivation of RASSF1A from region 3p21.3 in lung, breast and ovarian tumours," Oncogene 20(12):1509-18.
Agathanggelou et al. (2003) "Epigenetic inactivation of the candidate 3p21.3 suppressor gene BLU in human cancers," Oncogene 22(10):1580-8.
Agathanggelou et al. (2003) "Identification of novel gene expression targets for the Ras association domain family 1 (RASSF1A) tumor suppressor gene in non-small celllung cancer and neuroblastoma," Cancer Res. 63(17):5344-51.
Agathanggelou et al. (2005) "Role of the Ras-association domain family 1 tumor suppressor gene in human cancers," Cancer Res. 65(9):3497-508. Erratum in: Cancer Res. 65(12):5480.
Ahlquist et al (2000) "Colorectal Cancer Screening by Detection of Altered Human DNA in Stool: Feasibility of a Multitarget Assay Panel" Gastroenterology, 119:1219-1227.
Akino et al. (2005) "The Ras Effector RASSF2 is a Novel Tumor-Suppressor Gene in Human Colorectal Cancer." Gastroenterology, 129:156-169.
Alonzo et al. (2007) "Statistical methods for evaluating DNA methylation as a marker for early detection or prognosis," Disease Markers, 23:113-120.
Ausubel et al. (1995) Short Protocols in Molecular Biology, 3d ed., pp. 2-3-2-12, 3-30-3-33.
Azhikina et al (1996) "Factors affecting the priming efficiency of short contiguous oligonucleotide strings in the primer walking strategy of DNA sequencing" DNA Sequence—The Journal of Sequencing and Mapping, 6:211-216.
Beck (1987) "Colorimetric-detected DNA sequencing" Anal. Biochem., 164(2):514-520. Abstract only.
Behn et al. (1998) "Frequent detection of ras and p53 mutations in brush cytology samples from lung cancer patients by a restriction fragment length polymorphism-based "enriched PCR" technique," Clin Cancer Res. 4(2):361-71.
Behn et al. (1998) "Sensitive detection of p53 gene mutations by a 'mutant enriched' PCR-SSCP technique," Nucleic Acids Res. 26(5):1356-8.
Behn et al. (1998) "Simple and reliable factor V genotyping by PNA-mediated PCR clamping," Thromb Haemost. 79(4):773-7.
Bertario et al (1999) "Risk of Colorectal Cander Following Colonoscopic Polypectomy" Tumori, 85:157-162.
Beskin et al. (1995) "On the Mechanism of the Modular Primer Effect," Nucleic Acids Research, vol. 23, No. 15, ppo 2881-2885.
Blum H.E., (1995) "Colorectal Cancer: Future Population Screening for Early Colorectal Cancer" European Journal of Cancer, vol. 31A, pp. 1369-1372.
Bohm et al, (1997) Deletion Analysis at the DEL-27, APC and WS] Loci in Bladder Cancer: LOH at the DEL-27 Locus on 5p13-12 is a Prognostic, Int. J. Cancer (Pred. Oncol.) 74: 291.

(56) References Cited

OTHER PUBLICATIONS

Boom et al. (1990) "Rapid and Simple Method for Purification of Nucleic Acids," Journal of Clinical Microbiology, vol. 28, No. 3, pp. 495-503.
Bos et al, (1987) "Prevalence of ras Gene Mutations in Human Colorectal Cancers" Nature vol. 327, pp. 293-297.
Botstein et al. (1985) "Strategiesand Applications of in vitro Mutagenesis," Science, 229(4719):1193-1201.
Boynton et al. (2003) "DNA integrity as a potential marker for stool-based detection of colorectal cancer," Clinical Chemistry, 49(7):1058-1065.
Braun et al, (1997) "Improved Analysis of Microsatellites Using Mass spectrometry" Genomics, vol. 46, pp. 18-23.
Brenner et al. (2005) "Fecal DNA Biomarkers for the Detection of Colorectal Neoplasia: Attractive, but is it feasible?" Journal of the National Cancer Institute, 97(15):1107-1109.
Burbee et al. (2001) "Epigenetic inactivation of RASSF1A in lung and breast cancers and malignant phenotype suppression," J Natl Cancer Inst. 93(9):691-9.
Caetano-Anolles "Amplifying DNA with Arbitrary Oligonucleotide Primers," Cold Spring Harbor Laboratory Press, ISSN 1054-9803, pp. 85-94 (1993).
Caldas et al. (1994) "Detection of K-ras Mutations in the Stool of Patients with Pancreatic Adenocarcinoma and Pancreatic Ductal Hyperplasia" Cancer Research, vol. 54, pp. 3568-3573.
Capozzi et al. (1999) Evaluation of the Replication Error Phenotype in Relation to Molecular and Clinicopaihological Features in Hereditary and Early Onset Colorectal Cancee European Journal of Cancer 35:289-295.
Carothers et al. "Point Mutation Analysis in a Mammalian Gene: Rapid Preparation of Total RNA, PCR Amplification of cDNA, and Taq Sequencing by a Novel Method," 494 BioTechniques, vol. 7, pp. 494-499 (date unknown) Abstract only, (1989).
Cave et al. (1994) "Reliability of PCR Directly from Stool Samples: Usefulness of an Internal Standard," BioTechniques, vol. 16, No. 5, pp. 809-810.
Chambers et al. (1986) "The structure of the mouse glutathione peroxidase gene: the selenocysteine in the active site is encoded by the 'termination' codon, TGA" EMBO Journal 5(6):1221-1227. Abstract only.
Chapelle (1999) "Testing Tumors for Microsatellite Instability" European Journal of Human Genetics 7:407-408.
Charlesworth et al. (Sep. 15, 1994) "The Evolutionary Dynamics of Repetitive DNA in Eukaryotes," Nature, vol. 371, pp. 215-220.
Chen et al. (1985) "Supercoil Sequencing: A Fast and Simple Method for Sequencing Plasmid DNA" DNA, 4(2):165-170.
Chen et al. (1997) "Fluorescence Energy Transfer Detection as a Homogeneous DNA Diagnostic Method," Proc. Natl Acad. Sci., vol. 97, pp. 10756-10761.
Chen et al. (1997) "Microsatellite Instability in Sporadic-Colon-Cancer Patients With and Without Liver Metastases" International Journal of Cancer, 74:470-474.
Chen et al. (1997) "Template-Directed Dye-Terminator Incorporation (TDI) Assay: A Homogeneous DNA Diagnostic Method Based on Fluorescence Resonance Energy Transfer," Nucleic Acids. Research, vol. 25, No. 2, pp. 347-353.
Chen et al. (2005) "Detection in fecal DNA of colon cancer-specific methylation of the nonexpressed vimentin gene," J Natl Cancer Inst. 97:1124-1132.
Coughlin et al. (1999) "Public Health Perspectives on Testing for Colorectal Cancer Susceptibility Genes" American Journal of Preventive Medicine, 16:99-104.
Cunningham C. and M.G. Dunlop, (1996) "Molecular Genetic Basis of Colorectal Cancer Susceptibility," British Journal of Surgery vol. 83, pp. 321-329.
Dallol et al. (2004) "RASSF1A interacts with microtubule-associated proteins and modulates microtubule dynamics," Cancer Res. 64(12):4112-6.

Dammann et al. (2000) "Epigenetic inactivation of a RAS association domain family protein from the lung tumour suppressor locus 3p21.3." Nat Genet. 25(3):315-9.
Deng et al., (1996) "Loss of Heterozygosity in Normal Tissue Adjacent to Breast Carcinomas," Science. vol. 274, pp. 2057-2059.
Deuter et al. (1995) "A Method for Preparation of Fecal DNA Suitable for PCR," Nucleic Acids Research, vol. 23, No. 18, pp. 3800-3801.
Dib et al. (1996) "A Comprehensive Genetic Map of the Human Genome Based on 5,264 Microsatellites," Nature vol. 380, pp. 152-154.
Downward (2002) "Targeting RAS signalling pathways in cancer therapy," Nat Rev Cancer. 3(1):11-22.
Downward (2003) "Cell biology: metabolism meets death," Nature. 424(6951):896-7.
Downward (2003) "Role of receptor tyrosine kinases in G-protein-coupled receptor regulation of Ras: transactivation or parallel pathways?" Biochem J. 376(Pt 3):e9-10.
Dreijerink et al. (2001) "The candidate tumor suppressor gene, RASSF1A, from human chromosome 3p21.3 is involved in kidney tumorigenesis," Proc Natl Acad Sci USA, 98(13):7504-9.
Driscoll el al (1989) "An in Vitro System for the Editing of Apolipoprotein B mRNA" Cell, 58:519-525.
Duffy (1995) "Can Molecular Markers Now be Used for Early Diagnosis of Malignancy?" Clin. Chem. vol. 41, No. 10, pp. 1410-1413.
Eckfeld et al. (2004) "RASSF4/AD037 is a potential ras effector/tumor suppressor of the RASSF family," Cancer Res. 64(23):8688-93.
Eguchi et al. (1996) "Mutations of the p53 Gene in the Stool of Patients with Resectable Colorectal Cancer," Cancer Supplement, vol. 77, No. 8, pp. 1707-1710.
Enari et al. (1998) "A Caspase-Activated DNase that Degrades DNA During Apoptosis, and its Inhibitor ICAD," Nature, vol. 391, pp. 43-50.
Endoh et al. (2005) "RASSF2, a potential tumor suppressor, is silenced by CpG island hypermethylation in gastric cancer," British Journal of Cancer, 93:1395-1399.
England et al. (1978) "3'-Terminal labeling of RNA with T4 RNA ligase," Nature 275:560-561.
Erickson et al.(2001) "One base sequencing (OBS): an improved method for accurate SNP scoring," Human Genome Meeting (HGM).
Erster et al, (1988) "Use of Rnase H and primer extension to analyze RNA splicing," Nucleic Acids Res., 16(13):5999-6014.
European Search Report for EP Application 09167115.6 dated Sep. 16, 2009.
Fabian et al,. (1989) "Allele-specific expression of the murine Ren-1 genes," J. Biol. Chem. 264(29):17589-17594.
Fearon (1995) "16 Molecular Abnormalities in Colon and Rectal Cancer," The Molecular Basis of Cancer, pp. 340-357.
Fearon et al. (1990) "A genetic model for colorectal tumorigenesis," Cell. 61(5):759-67.
Feng et al. (2006) "Molecular Biomarkers for Cancer Detection in Blood and Bodily Fluids," Critical Reviews in Clinical Laboratory Sciences, 43(5-6):497-560.
Fournie et al. (1995) "Plasma DNA as a Marker of Cancerous Cell Death. Investigations in Patients Suffering from Lung Cancer and in Nude Mice Bearing Human Tumours," Cancer Letters, 91:221-227.
Frangi et al. (1991) "Nonsense Mutations Affect CI Inhibitor Messenger RNA Levels in Patients with Type I Hereditary Angioneurotic Edema," J. Clinical Invest. 88:755-759.
Fu et al. (1995) "A DNA Sequencing Strategy That Requires Only Five Bases of Known Terminal Sequence for Priming," Proc. NatL Acad Sci. USA, 92: pp. 10162-10166.
Galinsky et al. (1988) "Molecular cloning and sequence analysis of the human parainfluenza 3 virus gene encoding the L protein," Virology, 165(2):499-510.
Gao et al. (1988) "Restriction primer extension method of labeling oligonucleotide probes and its application to the detection of Hb E genes," Hemoglobin, 12(5-6):691-697.
Gardner et al. (2002) "Acyclic and dideoxy terminator preferences denote divergent sugar recognition by archaeon and Taq DNA polymerases," Nucleic Acids Research, 30(2):605-613.

(56) References Cited

OTHER PUBLICATIONS

Giacona et al. (1998) "Cell-Free DNA in Human Blood Plasma: Length Measurements in Patients with Pancreatic Cancer and Healthy Controls," Pancreas, vol. 17, No. 1, pp. 89-97.
Gismondi et al. (1997) "Characterization of 19 Novel and Sic Recuroing APC Mutations in Italian Adenomatous Polyposis Patients, Using Two-Different Mutation Detection Techniques" Human Mutation, vol. 9, No. 4, pp. 370-373.
Godson, (1980) "Primed synthesis methods of sequencing DNA and RNA" Fed. Proc.. 39(10):2822-2829.
Green et al. (1980) "Targeted deletions of sequences from closed circular DNA," Proc. Natl. Acad. Sci. 77(5):2455-2459.
Greene et al. (2001) "A Novel Method for SNP Analysis Using Fluorescence Polarization," Perkin Elmer Life Sciences.
Grossman et al. (1988) "Colonoscopic Screening of persons With Suspected Risk Factors for Colon Cancer" Gastmenterologv 94:395-400.
Gyllensten et al. (1995) "Sequencing of In Vitro Amplified DNA," Recombinant DNA Methodology II, (Wu, ed.) pp. 565-578.
Hasegawa et al. (1995) "Detection of K-ras Mutations in DNAs Isolated From Feces of Patients with Colorectal Tumors by Mutant-Allele-Specific Amplification (MASA)" Oncogene, vol. 10, pp. 1441-1445.
Herman (2002) "Hypermethylation pathways to colorectal cancer. Implications for prevention and detection," Gastroenterol Clin North Am. 31(4):945-58.
Herman JG, et al. (1996) "Methylation-specific PCR: A novel PCR assay for methylation status of CpG islands," Proc Natl Acad Sci USA 93:9821-9826.
Hesson et al. (2003) "NORE1A, a homologue of RASSF1A tumour suppressor gene is inactivated in human cancers," Oncoqene. 22(6):947-54.
Hesson et al. (2004) "Frequent epigenetic inactivation of RASSF1A and BLU genes located within the critical 3p21.3 region in gliomas," Oncogene 23( 3):2408-19.
Hesson et al. (2005) "CpG island promoter hypermethylation of a novel Ras-effector gene RASSF2A is an early event in colon carcinogenesis and correlates inversely with K-ras mutations," Oncogene 24:3987-3994.
Hickman et al. (1994) "Apoptosis and cancer chemotherapy," Phil. Trans R. Soc. Lond., 345:319-325.
Hoang et al. (1997) "BAT-26, an Indicator of the Replication Error Phenotype in Colorectal Cancers and Cell Lines" Cancer Research 57: 300-303.
Hollstein et al. (1991) "p53 Mutations in Human Cancers," Science, vol. 253, pp. 49-53.
Homes et al. (1990) "Emerging Techniques: Magnetic DNA Hybridization Properties of Oligonucleotide Probes Attached to Superparamagnetic Beads and Their Use in the Isolation of Poly(A) mRNA From Eukaryotic Cells," GATA 7(6):145-150.
Honchel et al. (1995) "Genomic Instability in Neoplasia," Seminars in Cell Biologv, vol. 6, pp. 45-52.
Hass et at, (1992) "Excrement Analysis by PCR" Scientific Correspondence pp. 199.
Hunkapiller et al. (1984) "A microchemical facility for the analysis and synthesis of genes and proteins," Nature 310:305-311.
Iacopetta et al. (1998) "Rapid and Nonisotopic SSCP-based Analysis of the BAT-26 Mononucleotide Repeat for Identification of the Replication Error Phenotype in Human Cancers," Human Mutation 12:355-360.
Iino et al. (1999) "DNA Microsatellite Instability in Hyperplastic Polyps, Serrated Adenomas, and Mixed Polyps: a Mild Mutator Pathway for Colorectal Cancer?" Journal of Clinical Pathology 52: 5-9.
Ikonen et al. "Quantitative Determination of Rare mRNA Species by PCR and Solid-phase Minisequencing," Cold Spring Harbor Laboratory Press, ISSN 1054-8903, pp. 234-240 (1992).
Iniesta et al. (1998) "Genetic Abnormalities and Microsatellite Instability in Colorectal Cancer" Cancer Detection and Prevention 22:383-395.

International Searcg Report for PCT/US99/08849 (Sep. 13, 1999).
International Search Report for PCT/US03/04827 (Sep. 4, 2003).
International Search Report for PCT/US05/016518, (Jul. 4, 2006).
International Search Report for PCT/US05/30942, (Jul. 20, 2006).
International Search Report for PCT/US05/39670 (Apr. 12, 2006).
Irimia et al. (2004) "CpG island promoter hypermethylation of the Ras-effector gene NORE1 A occurs in the context of a wild-type K-ras in lung cancer," Oncogene. 23(53):8695-9.
Ishimaru et al. (1995) "Microsatellite Instability in Primary and Metastatic Colorectal Cancers" International Journal of Cancer 64:153-157.
Iwaya et al. (1998) "Infrequent Fratneshift Mutations of Polynucleotide Repeats in Multiple Primary Cancers Affecting the Esophagus and Other Organs" Genes, Chrom & Cancer 23:317-322.
Jack et al. (2002) "Kicking the Sugar Habit: AcyNTP Terminator Incorporation by Vent DNA Polymerase" HGH2002 Poster Abstracts: 12. New Technologies, Poster No. 621, Abstract only.
Jarvinen et al. (1995) "Screening Reduces Colorectal Cancer Rate in Families With Hereditary Nonpolyposis Colorectal Cancer" Gastroenterology 108: 1405-1411.
Jeffreys et al. (2003) "DNA enrichment by allele-specific hybridization (DEASH): a novel method for haplotyping and for detecting low-frequency base substitutional variants and recombinant DNA molecules," Genome Research, 13:2316-2324.
Jernvall et al. (1999) "Microsatellite Instability: Impact on Cancer Progression in Proximal and Distal Colorectal Cancers" European Journal of Cancer 35:197-201.
Jessup et al. (1992) "The Biology of Colorectal Carcinoma," Current Problems in Cancer pp. 263-328.
Jonsson et al. (1995) "From Mutation Mapping to Phenotype Cloning," Proc. Natl. Acad. Sci., vol. 92 pp. 83-85.
Kainz et al. (1989) "A modified primer extension procedure for specific detection of DNA-RNA hybrids on nylon membranes," 179(2):366-370, Abstract only.
Kawakami et al. (2000) "Hypermethylated APC DNA in Plasma and Prognosis of Patients with Esophageal Adenocarcinoma," Journal of the National Cancer Institute, 92(22):1805-1811.
Khokhlatchev et al. (2002) "Identification of a novel Ras-regulated proapoptotic pathway," Curr Biol. 12(4):253-65.
Kieleczawa et al. (1992) "DNA Sequencing by Primer Walking with Strings of Contiguous Hexamers," Science,258: pp. 1787-1791.
Kim et al. (2006) "CpG island methylation of genes accumulates during the adenoma progression step of the multistep pathogenesis of colorectal cancer," Genes Chromosomes Cancer 45:781-789.
Kim et al. (1998) Microsatellite Instability in Young Patients With Colorectal Cancee Pathology International 48: 586-594.
Ko et al. (1999) "Genomic Instability and Alterations in Apc, Mcc and Dcc in Hong Kong Patients with Colorectal Carcinoma," Int. J. Cancer (Pred. Onco1.1, 84:404-409.
Komher at al. (1989) "Mutation detection using nucleotide settings that alter electrophoretic mobility," Nucleic Acids Research, 17(19):7779-7784.
Kondo et al. (2004) "Epigenetic changes in colorectal cancer," Cancer Metastasis Rev. 23(1-2):29-39.
Konishi et al. (1996) "Molecular Nature of Colon Tumors in Hereditary Nonpolyposis Colon Cancer, Familial Polyposis, and Sporadic Colon Cancer" Gastroenterology 1 1 I : 307-317.
Kotler et al. (1993) "DNA Sequencing: Modular Primers Assembled from a Library of Hexamers or Pentamers," Proc. Natl. Acad Sci. USA, 90: pp. 4241-4245 (May 1993).
Krook et al. (1992) "Rapid and simultaneous detection of multiple mutations by pooled and multiplex single nucleotide primer extension: application to the study of insulin-responsive glucose transporter and insulin receptor mutations in non-insulin-dependent diabetes," Human Molecular Genetics, vol. 1, No. 6, pp. 391-395.
Kuppuswamy et al (1991) "Single Nusleotide primer extension to detect genetic diseases: Experiemental application to hemophilia B (factor IX) and Cystic fibrosis genes," Proc. Natl. Acad. Sci., 88:1143-1147.
Lamberti et al. (1999) "Microsatellite Instability—a Useful Diagnostic Tool to Select Patients at High Risk for Hereditary Non-Polyposis Colorectal Cancer: A Study in Different Groups of Patients With Colorectal Cancer" Gut 44:839-843.

(56) References Cited

OTHER PUBLICATIONS

Lebacq (1992) "Polymerase chain reaction and other methods to detect hot-spot and multiple gene mutations," Advances in Clinical Biology, vol. 50, pp. 709-712.

Lee et al, (1992) DNA sequencing with dye-labeled terminators and T7 DNA polymerase: effect of dyes and dNTPs on incorporation of dye-terminators, Nucl. Acids Res. 20: 2471.

Lengauer et al. (1998) "Genetic Instabilities in Human Cancers," Nature, vol. 396, pp. 643-649.

Leong et al. (1993) "Detection of MYCN Gene Amplification and Deletions of Chromosome Ip in Neuroblastoma by In Situ Hybridization Using Routine Histologic Sections," Laboratov Investigations, vol. 69, No. 1, pp. 43-50.

Lerman et al. (2000) "The 630-kb lung cancer homozygous deletion region on human chromosome 3p21.3: identification and evaluation of the resident candidate tumor suppressor genes. The International Lung Cancer Chromosome 3p21.3 Tumor Suppressor Gene Consortium," Cancer Res. 60(21):6116-33.

Lin et al. (1998) "Colorectal and Extracolonic Cancer Variations in MLHI/MSH2 Hereditary Nonpolyposis Colorectal Cancer Kindreds and the General Population" Diseases of the Colon & Rectum 41:428-433.

Lipkin et al. (1998) "Quantitative Trait Locus Mapping in Dairy Cattle by Means of Selective Milk DNA Pooling Using Dinucleotide Microsatellite Markers: Analysis of Milk Protein Percentage" Genetics 49:1557-1567.

Litia et al. (1992) "Simultaneous Detection of Two-Cystic Fibrosis Alleles Using Dual-Label Time-Resolved Fluorometry," Molecular and Cellular Probes, vol. 6, pp. 505-512.

Liu et al. (2003) "Control of microtubule stability by the RASSF1 A tumor suppressor," Oncogene. 22(50):8125-36.

Liu et at, (1986) "Synthesis of a fixed-length single-stranded DNA probe by blocking primer extension in bacteriophage M13," Gene, 42:113-117.

Lleonart et al. (1998) "Microsatellite Instability and p53 Mutations in Sporadic Right and Left Colon Carcinoma" American Cancer Society 83:889-895.

Lo et al. (1984) "Specific amino acid substitutions in bacterioopsin: Replacement of a restriction fragments containing altered codons," Proc. Natl. Acad. Sci., 81:2285-2289.

Loktionov A. and I. K. O'Neill, (1995) "Early Detection of Cancer-Associated Gene Alterations in DNA Isolated from Rat Feces During Intestinal Tumor Induction with 1,2-Dimethylhydrazine," International Journal of Oncology, vol. 6, pp. 437-445.

Loktionov et al. (1998) "Quantitation of DNA from Exfoliated Colonocytes Isolated from Human Stool Surface as a Novel Noninvasive Screening Test for Colorectal Cancer," Clinical Cancer Research, vol. 4, pp. 337-341.

Lathe, et al. (1998) "The APC Gene 11307K Variant is Rare in Norwegian Patients with Familial and Sporadic Colorectal or Breast Cancer" Cancer Research, vol. 58, pp. 2923-2924.

Luo et al, (1988) "Point mutations in glycoprotein gene of vesicular stomatitis virus (New Jersey serotype) selected by resistance to neutralization by epitope-specific monoclonal antibodies," Virology, 163(2):341-348.

Makristhathis et al. (1998) "Detection of *Helicobacter* pylori in Stool Specimens by PCR and Antigen Enzyme Immunoassay," Journal of Clinical Microbiology, vol. 36, No. 9, pp. 2772-2774.

Mao L. et al. (1996) "Molecular Detection of Primary Bladder Cancer by Microsatellite Analysis," Science. vol. 271, pp. 659-662.

Matteucci et al. (1981) "Studies on Nucleotide Chemistry IV. Synthesis of Deoxyoligonucleotides on a Polymer Support," J. Am. Chem. Soc., 103:3185-3191.

Maxam et al. (1977) "A new method for sequencing DNA," Proc. Natl. Acad. Sci., 74(2):560-564.

Medeiros et al. (1989) "M13 Bioprints: non-isotopic detection of individual-specific human DNA fingerprints with biotinylated M13 bacteriophage," Forensic Sci. Int., 43(3):275-280.

Meijers-Heijboer et al. (1999) "Familial Endometrial Cancer in Female Carriers of MSH6 Germline Mutations" Nature Genetics 23: 142-144.

Miller et al. (1997) "Semiautomated Resolution of Overlapping Stutter Patterns in Genomic Microsatellite Analysis" Analytical Biochemistry 251:50-56.

Mills, Stacey E. (2001) "Digital Diagnoses in an Analog World," American Society for Clinical Pathology Editorial, two pages.

Morinaga et al. (1984) "Improvement of Oligonucleotide-Directed Site-Specific Mutagenesis Using Double-Stranded Plasmid DNA," Biotechnology pp. 636-639.

Muller et al. (2004) "Methylation changes in faecal DNA: a marker for colorectal cancer screening?" Lancet. 363(9417):1283-5.

Myers, R.M. (1993) "The Pluses of Subtraction," Science. vol. 259, pp. 942-943.

Naber (1994) "Molecular Pathology—Detection of Neoplasia," New England Journal of Medicine, vol. 331, No. 22, pp. 1508-1510.

Netzer, P. et at, (1997) "Screening sigmoidoscopy or colosopy for detection of colorectal adenomas and cancers?" Gastroenterology, I12(4):A626, Citation Only.

Nikiforov et at, (1994) "Genetic Bit Analysis: a solid phase method for typing single nucleotide polymorphisms," Nucleic Acids Research, vol. 22, No. 20, pp. 4167-4175, Abstract only.

Nollau et al. (1996) "Detection of K-ras Mutations in Stools of Patients with Colorectal Cancer by Mutant-Enriched PCR," Int. J. Cancer, vol. 66 pp. 332-336.

Nollau et al. (1996) "Isolation of DNA from Stool and Bodily Fluids for PCR Amplication," BioTechniques, vol. 20, No. 5, pp. 784-788.

Olsen et al. (1989) "Incomplete primer extension during in vitro DNA amplification catalyzed by Taq polymerase; exploitation for DNA sequencing," Nucleic Acids Res . . . 17(23):9613-9620, Abstract only.

Olson et al. (2005) "DNA stabilization is critical for maximizing performance of fecal DNA based colorectal cancer tests," Diaqn Mol Pathol 14:183-191.

Orlow et al. (1995) "Deletion of the p16 and p15 Genes in Human Bladder Tumors Journal of the National Cancer Institute" vol. 87, No. 20, pp. 1524-1529.

Ortiz-Vega et al. (2002) "The putative tumor suppressor RASSF1 A homodimerizes and heterodimerizes with the Ras-GTP binding protein Nore1," Oncogene. 21(9):1381-90. Erratum in: Oncogene 21(12):1943.

Palmieri et al. (1999) "Polymerase Chain Reaction-Based Detection of Circulating Melanoma Cells as an Effective Marker of Tumor Progression," Journal of Clinical Oncology, 17(1): 304-311.

Park et al.(1999) "Gene-Environment Interaction in Hereditary Nonpolyposis Colorectal Cancer with Implications for Diagnosis and Genetic Testing" International Journal of Cancer 82: 516-519.

Parker et al. (1988) "Interaction of 2-Halogenated dATP analogs (F, CI and Br) with human DNA polymerases, DNA primase, and ribonucleotide reductase," Mol. Pharmacol., 34(4):485491, Abstract only.

Peattie, (1979) "Direct chemical method for sequencing RNA," Proc. Natl. Acad. Sci., 76(4):1760-1764.

Peltomaki et al (1997) "Mutations Predisposing to Hereditary Nonpolyposis Colorectal Cancer: Database and Results of a Collaborative Study" Gastroenterology 113: 1146-1158.

Perlin et al. (1995) "Toward Fully Automated Tenotyping: Genotyping Microsatellite Markers by Deconvolution" American Journal of Human Genetics 57:1199-1210.

Pharmacia (1991/1992) Molecular and Cell Biology Catalogue, pp. 8.3-8.6.

Pharmacia (1998) BioDirectorv, pp. 104-109.

Piao et al. (1997) "Relationship between Loss of Heterozygosity of Tumor Suppressor Genes and Histologic Differentiation in Hepatocellular Carcinoma," Cancer, vol. 80, No. 5, pp. 865-872.

Ponz de Leon et al. (1998) "Frequency and Type of Colorectal Tumors in Asymptomatic High Risk Individuals in Families with Hereditary Nonpolyposis Colorectal Cancer" Cancer Epidemiology, Biomarkers & Prevention 7: 639-641.

Ponz de Leon et al. (1999) "Hereditary Colorectal Cancer in the General Population: From Cancer Registration to Molecular Diagnosis" Gut 45: 32-38.

(56) References Cited

OTHER PUBLICATIONS

Praskova et al. (2004) "Regulation of the MST1 kinase by autophosphorylation, by the growth inhibitory proteins, RASSF1 and NORE1, and by Ras," Biochem J. 381(Pt 2):453-62.
Prober et al. (1987) "A System for Rapid DNA Sequencing with Fluorescent Chain-Terminating Dideoxynucleotides," Research Articles, pp. 336-341.
Pyatt et al. (1999) "Polymorphic Variation at the BAT-25 and BAT-26 Loci in Individuals of African Origin" American Journal of Pathology 155: 349-353.
Raff (1998) "Cell Suicide for Beginners," Nature, vol. 396, pp. 119-122.
Rashid et al. (1999) "Genetic Epidemiology of Mutated K-ras Proto-Oncogene, Altered Suppressor Genes, and Microsatellite Instability in Colorectal Adenomas" Gut 44: 826-833.
Ravelingien et al. (1995) "Contribution of Molecular Oncology in the Detection of Colorectal Carcinomas," Acta Gastro-Enterologica Belgica, vol. 58, pp. 270-273.
Rhyu (1996) Molecular Mechanisms Underlying Hereditary Nonpolyposis Colorectal Carcinoma, Journal of the National Cancer Institute, vol. 88, No. 5, pp. 240-251.
Rice et al. (2001) "Identification of single nucleotide polymorphisms (SNPs) and other sequence changes and estimation of nucleotide diversity in coding and flanking regions of the NMDAR1 receptor gene in schizophrenic patients," Molecular Psychiatry, 6(3):274-284.
Ridanpaa et al. (1995) Detection of Loss of Heterozygosity in the p53 Tumor Suppressor Gene Using a PCR-based Assay, Path. Res. Pract., vol. 191, pp. 399-402.
Riegler et al. (1999) "Prevalence of HNPCC in a Series of Consecutive Patients on the First Endoscopic Diagnosis of Colorectal Cancer: A Multicenter Study" Endoscopy 31: 337-341.
Rinaldy et al. (1988) "Gene Cloning Using cDNA Libraries in a Differential Competition Hybridization Strategy: Application to Cloning XP-A Related Genes," DNA 7(8):563-70.
Rodriguez-Bigas et al. (1997) "A National Cancer Institute Workshop on Hereditary NonpolyposisColorectal Cancer Syndrome: Meeting Highlights and Bethesda Guidelines" Journal of the National Cancer Institute 89:1758-1762.
Roemer et al (2000) "Sequencing BAC DNA With Near-Infrared Flourescent Non-Nucleotide Terminators," LI-COR On-line Poster 530, LI-COR, Inc., Biotechnology, Lincoln, Nebraska, nine pages.
Rosenthal et al. (1985) "Solid-phase methods for sequencing of nucleic acids, I. Simultaneous sequencing different oligodeoxyribonucleotides using a new, mechanically stable anion-exchange paper," Nucleic Acids Research, 13(4):1173-1184.
Runnebaum et a. (1994) "Multiplex PCR Screening detects small p53 deletions and insertions in human ovarian cancer cell lines," Human Genetics, vol. 93, pp. 620-624.
Salahshor et al. (1999) "Microsatellite Instability in Sporadic Colorectal Cancer is Not an Independent Prognostic Facto(" British Journal of Cancer 81: 190-193.
Sambrook et al. (1989) "Molecular Cloning," Second Edition, p. 13.67-13.69.
Samiotaki et al. (1994) "Dual-Color Detection of DNA Sequence Variants by Ligase-Mediated Analysis," Genomics 20:238-42.
Samowitz et al. (1995) "Microsatellite Instability in Human Colonic Cancer Is Not a Useful Clinical Indicator of Familial Colorectal Cancer" Gastroenterology 109: 1765-1771.
Samowitz et al. (1997) "Microsatellite Instability in Colorectal Adenomas" Gastroenterology 112: 1515-1519.
Samowitz et al. (1999) "BAT-26 and BAT-40 Instability in Colorectal Adenomas and Carcinomas and Germline Polymorphisms" American Journal of Pathology 154:1637-1641.
Samuels et al. (2004) "High frequency of mutations of the PIK3CA gene in human cancers," Science, 304(5670):554.
Sanger et al. (1975) "A Rapid Method for Determing Sequences in DNA by Primed Synthesis with DNA Polymerase " J. Mol. Biol . . . 94:441-448.
Sanger et al. (1977) "DNA Sequencing with Chain-Terminating Inhibitors" Proc. Natl. Acad. Sci. USA, vol. 74, No. 12, pp. 5463-5467.
Segel (1976) "Double Label Analysis," Biochemical Calculations, 2d ed., pp. 373-376.
Sheehan et al. (1987) "Reducing agent-sensitive dimerization of the hemagglutinin-neuraminidase glycoprotein of Newcastle disease virus correlates with the presence of cycteine at residue 123," Virology, 161(2):603-606.
Shitoh et al. (1998) "Important Microsatellite Markers in the Investigation of RER in Colorectal Cancers," Jim. J. Cli, Oncol vol. 28, No. 8, pp. 538-541.
Shivakumar et al. (2002) "The RASSF1A tumor suppressor blocks cell cycle progression and inhibits cyclin D1 accumulation," Mol Cell BioL 22(12):4309-18.
Shortle et al, (1980) "Segment-directed mutagenesis: Construction in vitro of point mutations limited to a small predetermined region of a circular DNA molecule," Proc. Natl. Acad. Sci., 77(9):5375-5379.
Shortle et al. (1981) "Directed Mutagenesis," Ann. Rev. Genet. 15:265-294.
Shortle et al. (1982) "Gap misrepair mutagenesis: Efficient site-directed induction of transition, transversion, and frameshift mutations in vitro," Proc. Natl. Acad. Sci., 79:1588-1592.
Shumaker et al. (1996) "Mutation Detection by Solid Phase Primer Extension," Human Mutation, vol. 7, pp. 346-354.
Sidransky et al. (1992) "Identification of ras Oncogene Mutations in the Stool of Patients with Curable Colorectal Tumors," Science, vol. 256, pp. 102-105.
Singer et al. (1989) "Effect of 3' flanking neighbors on kinetics of pairing of dCTP or dTTP opposite O6-methylguanine in a defined primed oligonucleotide when Escherichia coli DNA polymerase I is used," Proc. Natl. Acad. Sci., 86:8271-8274.
Singer-sam et al. (1992) "A Sensitive, Quantitative Assay for Measurement of Allele-specific Transcripts Differing by a Single Nucleotide," PCR Methods and Applications. 1:160-163.
Smith-Ravin et al. (1995) "Detection of c-Ki-ras Mutations in Fecal Samples from Sporadic Colorectal Cancer Patients," Gut, vol. 36, pp. 81-86.
Sokolov, (1989) "Primer extension technique for the detection of single nucleotide in genomic DNA,"Nucleic Acids Research, 18(12):3671.
Srinivas et al. (2001) "Trends in biomarker research for cancer detection," The Lancet, 2: 698-704.
Stahl et al. (1988) "Solid phase DNA sequencing using the biotin-avidin system," Nucleic Acids Research, 16(7):3025-3038.
Suzuki et al. (2002) "A genomic screen for genes upregulated by demethylation and histone deacetylase inhibition in human colorectal cancer," Nat Genet 31(2):141-9. Epub May 6, 2002.
Syngal et al. (1998) "Benefits of Colonoscopic Surveillance and Prophylactic Colectomy in Patients With Hereditary Nonpolyposis Colorectal Cancer Mutations," Annals of Internal Medicine 129: 787-796.
Syngal et al. (1999) "Interpretation of Genetic Test Results for Hereditary Nonpolyposis Colorectal Cancer" JAMA 282: 247.
Syvanen (1994) Detection of Point Mutations in Human Genes by the Solid-phase Minisequencing Method, Clinica Chimica Acta, vol. 226, pp. 225-236, Abstract Only.
Syvanen et al. (1990) "A primer-Guided Nucleotide Incorporation Assay in the Genotyping of Apolipoprotein E," Genomics, 8:684-692.
Tagore et al. (2003) "Sensitivity and Specificity of a Stool DNA Multitarget Assay Panel for the Detection of Advanced Neoplasia," Clinical Colorectal Cancer, 3(1):47-53.
Takeda et al. (1993) "Detection of K-ras Mutation in Sputum by Mutant-Allele-Specific Amplification (MASA)" Human Mutation, vol. 2, pp. 112-117.
Thibodeau et al. (1993) "Microsatellite Instability in Cancer of the Proximal Colon," Science, vol. 260, pp. 816-819.
Thiede et al. (1996) "Simple and sensitive detection of mutations in the ras proto-oncogene using PNA-mediated PCR clamping," Nucleic acids research, 24:983-984.

(56) References Cited

OTHER PUBLICATIONS

Tommasi et al. (2002) "RASSF3 and NORE1: identification and cloning of tWO-human homologues of the putative tumor suppressor gene RASSF1" Oncogene. 21(17):2713-20.

Toyota et al. (1999) "CpG island methylator phenotype in colorectal cancer," Proc Nat. Acad Sci USA 96:8681-8686.

Traverso et al. (2002) "Detection of APC Mutations in Fecal DNA from Patients with Colorectal Cancer," N Engl. J. Med . . . 346(5):311-320.

Ugozzoli, et al, "Detection of Specific Alleles by Using Allele-Specific Primer Extension Followed by Capture on Solid Support," CATA 9(4): pp. 107-112 (1992).

van Engeland et al. (2002) "K-ras mutations and RASSF1A promoter methylation in colorectal cancer," Oncogene. 21(23):3792-5.

Vasen et al. (1993) "Surveillance in Hereditary Nonpolyposis Colorectal Cancer: An International Cooperative Study of 165 Families" Diseases of the Colon & Rectum) 36:1-4.

Vasen et al. (1998) "A Cost-Effectiveness Analysis of Colorectal Screening of Hereditary Nonpolyposis Colorectal Carcinoma Gene Carriers" American Cancer Society 82:1632-1637.

Vasen et al. (1999) "New Clinical Criteria for Hereditary Nonpolyposis Colorectal Cancer (HNPCC, Lynch Syndrome) Proposed by the International Collaborative Group on HNPCC" Gastroenterology, 116:1453-1456.

Vavvas et al. (1998) "Identification of Nore1 as a potential Ras effector," J Biol Chem. 273(10):5439-42.

Villa et al. (1996) "Identification of Subjects at Risk for Colorectal Carcinoma Through a Test Based on K-ras Determination in the Stool," Gastroenterology, vol. 110, No. 5, pp. 1346-1353.

Vogelstein, B. and Kinzler, K.W., (1999) "Digital PCR," Proc. NatL Acad. Sci. USA, vol. 96, pp. 9236-9241.

Vos et al. (2003) "RASSF2 is a novel K-Ras-specific effector and potential tumor suppressor," J Biol Chem. 278(30):28045-51.

Vos et al. (2004) "A role for the RASSF1 A tumor suppressor in the regulation of tubulin polymerization and genomic stability," Cancer Res. 64(12).4244-50.

Vreeland et al. (2002) "Multiplexed, High-Throughput Genotyping by Single-Base Extension and End—Labeled Free-Solution Electrophoresis," Anal. Chem. 74:4328-4333.

Wada et al. (1983) "Automatic DNA sequencer: Computer-programmed microchemical manipulator for the Maxam-Gilbert sequencing method," Rev__ Sci. Instrum., 54(11):1569-1572.

Wagner et al. (2002) "Frequent RASSF1A tumour suppressor gene promoter methylation in Wilms' tumour and colorectal cancer," Oncoqene. 21 (47):7277-82.

Wallace et al. (1979) "Hybridization of Synthetic Oligodeoxyribonucleotides to <DT 174 DNA: the Effect of Single Base Pair Mismatch," Nucleic Acids Research, vol. 6, No. 11, pp. 3543-3557.

Walsh et al. (1996) "Sequence Analysis and Characterization of Stutter Products at the Tetranucleotide Repeat Locus vWA," Nucleic Acids Research vol. 24, No. 14, 2807-2812.

Walsh et al. (1992) "Preferential PCR Amplification of Alleles: Mechanisms and Solutions," PCR Methods and Applications, pp. 241-250.

Wang et al. (1998) Large-Scale Identification, Mapping, and Genotyping of Single Nucleotide Olymorphisms in the Human Genome, Science, vol. 280, pp. 1077-1082.

Watson et al. (1994) "Isolation of Differentiality Expressed Sequence Tags from Human Breast Cancer," Advances in Brief XP 000576043 pp. 4598-4602.

Whitney et al. (2004) "Enhanced retrieval of DNA from human fecal samples results in improved performance of colorectal cancer screening test," J Mol Diagn. 6:386-395.

Written opinion for PCT/US05/30942, (Jul. 26, 2006).

Young G.P., and B.H. Demediu, (1992) "The Genetics, Epidemiology, and Early Detection of Gastrointestinal Cancers" Current Opinion in Oncology, vol. 4, pp. 728-735.

Zakour et al. (1984) "Site specific mutagenesis: insertion of single noncomplementary nucleotides at specified sites by error-directed DNA polymerization," Nucleic Acids Research, 12(16):6615-6628.

Zhang et al. (2006) "Inactivation of RASSF2A by promoter methylation correlates with lymph node metastasis in nasopharyngeal carcinoma," International Journal of Cancer, 120:32-38.

Zhou et al. (1997) "Allelic Profiles of Mononucleotide Repeat Microsatellites in Control Individuals and in Colorectal Tumors With and Without Replication Errors" Oncoeene 15: 1713-1718.

Zhou et al. (1998) "Determination of the Replication Error Phenotype in Human Tumors Without the Requirement for Matching Normal DNA by Analysis of Mononucleotide Repeat Microsatellites" Genes. Chromosomes & Cancer 21: 101-107.

Zimmem et al. (1978) "3'-Terminal nucleotide sequence of encephalomyocarditis virus RNA determined by reverse transcriptase and chain-terminating inhibitors," Proc. Natl. Acad. Sci., 75:4257-4260.

Zitt et al. (2007) "DNA methylation in colorectal cancer," Disease Markers 23(1-2):51-71.

Zoller et al. (1982) "Oligonucleotide-directed mutagenesis using M13-derived vectors: an efficient and general procedure for the production of point mutations in any fragment of DNA," Nucleic Acids Research, 10(20):6487-6500.

"Written Opinion", PCT/US05/39670, Apr. 12, 2007.

* cited by examiner

METHOD FOR MONITORING DISEASE PROGRESSION OR RECURRENCE

RELATED APPLICATIONS

This application is a national stage filing under 35 U.S.C. §371 of PCT International application PCT/US2005/039670 designating the United States of America, and filed Oct. 27, 2005, the entire contents of which are hereby incorporated herein by reference. This application claims the benefit under 35 U.S.C. §119(e) to U.S. Provisional Application No. 60/627,248, filed on Nov. 12, 2004, and U.S. Provisional Application No. 60/623,005, filed on Oct. 27, 2004, the entire contents of both of which are hereby incorporated herein by reference.

FIELD OF THE INVENTION

The invention relates generally to methods for detecting and monitoring diseases using nucleic acid-based markers.

BACKGROUND OF THE INVENTION

An impediment in the development of anti-cancer modalities is the dearth of methods for evaluating the effectiveness of such treatments. Accordingly, there has been interest in finding biomarkers and other surrogate endpoints that may substitute for clinical endpoints, especially for the evaluation of treatments whose outcomes do not become evident for many years. However, limitations of current surrogate endpoint validation techniques include a general failure in predicting outcome in treating diseases that are multifactorial in terms of the physiological and/or behavioral changes that may occur in populations suffering from the disease. Thus, there is currently a need to develop more effective techniques for identification of surrogate endpoints, for surrogate endpoint analysis, for using surrogate endpoints in clinical trials of experimental treatment regimens, and for monitoring the effectiveness of established treatment regimens in the practice of medicine.

SUMMARY OF THE INVENTION

Aspects of the invention relate to methods and compositions for detecting and/or genetically characterizing diseased tissue (e.g., diseased cells) in a patient. In certain aspects, information about the diseased tissue may be used to monitor disease progression, regression, recurrence, and/or response to treatment.

In one aspect, the invention provides a method for detecting the presence of a tumor in a subject. The method includes contacting a tumor sample from the subject with a plurality of tumor markers, diagnosing the presence of a tumor in the subject based on the presence of at least one tumor marker from the plurality. One or more of the tumor markers from the plurality of markers that reveal the presence of the tumor is then tested in a biological sample from the patient. The presence of the tumor marker in the biological sample indicates a tumor is present in the subject. The subject can be, e.g., a human, a non-human primate, dog, cat, cow, horse, pig, rodent (including a rat or mouse). In some embodiments, the method included treating the tumor in the subject prior to testing the biological sample. The treatment can be, e.g., surgery, radiation, or chemotherapy. If desired, the biological sample may also be tested prior to beginning treatment. This sample provides a reference for comparing the presence of the tumor markers in the biological sample during or after treatment of the tumor. In some embodiments, the plurality of tumor markers has a sensitivity for detecting the tumor in the subject of at least 50%, 75%, 80%, 85%, 90%, 95%, 98%, or 99%. In some embodiments, one or more markers in the plurality detects a nucleic acid sequence substitution, deletion, insertion or alteration in nucleic acid stability in a nucleic acid stability assay. The tumor can be, e.g., lung cancer, prostate cancer, bladder cancer, colorectal cancer, pancreatic cancer, gastric cancer, breast cancer, ovarian cancer, endometrial, soft tissue sarcoma, osteosarcoma, hepatocellular carcinoma, lymphoma, or a leukemia. In some embodiments, the marker detects 1, 5, 10 15 or 20 or mutations in an adenomatous polyposis coli (APC), p53, or K-ras gene. Alternatively, or in addition, the marker can detects a microsatellite instability marker (BAT-26), or a marker of abnormal apoptosis (DNA Integrity Assay). The biological sample can be, e.g., blood, plasma, serum, cerbrospinal fluid, lymph, tear, semen, urine, sweat, sputum, bronchiolar lavage, abuccal swab product, or cervical smear. In some embodiments, the biological sample is detected using allele-specific PCR or mismatch amplification mutation analysis. In some embodiments, the method further includes testing the biological sample for the presence of the tumor prior to treating the tumor. Also within the invention is a method for monitoring the recurrence of a tumor in a subject. The method includes contacting a tumor sample from the subject with a plurality of tumor markers and diagnosing the presence of a tumor in the subject based on the presence of at least one tumor marker from the plurality of markers. The subject is then treated to remove or reduce the tumor, and a biological sample from the subject is tested with the at least one tumor marker that was used to diagnose the tumor.

In one embodiment, the invention provides a clinical algorithm for personalized monitoring of the course of a tumor and its treatment in a given patient. A tumor is diagnosed in a first step using a collection of markers that can reveal the presence of the tumor. By using a sufficiently high number of markers, sensitivity of diagnoses can be very high. The sensitivity offered by the collection of markers is exploited in a second step by using those marker or markers that were used to reveal the presence of the tumor to monitor the progression of the tumor. The monitoring can be prior to treatment, during treatment, or following treatment. Thus, the method can be used to monitor the progression, spread, treatment, metastasis, and/or recurrence of the tumor.

In a first step of this embodiment, an assay may be performed to identify specific genetic markers, or mutations, that are indicative of the presence of a tumor. The first step is typically performed with a plurality of markers that in aggregate provide for a highly sensitive test for detecting a tumor. In some embodiments, the presence of a marker previously known to be associated with a tumor indicates the presence of tumor in a subject. In other embodiments, the presence of a marker in the tumor sample and the absence of the marker in a biological sample (e.g., biological fluid, organ, or tissue) known to lack the tumor indicates the presence of a tumor in the subject.

Markers indicative of the presence of a tumor can be detected by using any method known in the art, including by reference to a nucleotide database, such as GenBank, EMBL, or any other appropriate database, by gel electrophoresis, or by other standard methods. In some embodiments, the regions considered are regions in which loss of heterozygosity is prevalent, such as regions containing tumor suppressor genes.

In a second step the marker or markers associated with the tumor in the first step are used to determine whether the tumor (either the original or a metastasis of a primary tumor) is present in a biological sample. The biological sample is typically not from the same tissue as that from the sample in which the original tumor was diagnosed. However, it is typically a sample that is easily isolated, provided that tumor-associated DNA, if present in the subject, can be detected in the sample. The second step is typically performed at some time following the initial detection of the tumor. Thus, the second step can be performed at any later point in time to monitor the growth of a tumor diagnosed in the first step of the method. Alternatively, the second step can be performed during or following treatment (e.g., following surgery, radiation and/or chemotherapy) of a tumor. The presence of the marker associated with the presence of the tumor indicates the tumor is still present in the subject, whereas a reduction or absence of the marker indicates the tumor has regressed or disappeared from the subject. The first and second steps can be performed as many times as desired in order to confirm the diagnosis of a tumor—in a subject, or to monitor its continued presence.

A tumor sample can be tested from a patient who has a tumor or cancer, or is suspected of having a tumor or cancer. Tumors or cancers suitable for use in the method include, e.g., colorectal cancer, breast cancer, lung cancer, prostate cancer, bladder cancer, colorectal cancer, pancreatic cancer, gastric cancer, breast cancer, ovarian cancer, endometrial, soft tissue sarcoma, osteosarcoina, hepatocellular carcinoma. In the case of lymphomas and leukemias, a sample containing lymphocytes, leukemic cells, or lymph tissues is typically obtained. Suitable cell samples include, but are not limited to, tissue from a growth suspected or known to be cancerous, tissue adjacent to a resection of a tumor, and tissue distant from the site of a tumor, such as lymph nodes which are suspected of bearing metastatic cells.

In general, any set of markers that can identify the presence of a tumor can be used. In some embodiments, the marker set has a sensitivity of at least 50%, 75%, at least 80%, 85%, 90%, 95%, 98%, or 99%. The term "sensitivity" relates to the incidence of false negative results, i.e., to the probability that an individual in which a given mutation is present will be correctly identified. A test which has "high sensitivity" has few, e.g., fewer than 1% false negative results, and thus will rarely if ever miss the presence of a mutation, although it may provide an incorrect diagnosis for the presence of the mutation. For comparison, the term "specificity" relates to the incidence of false positive results in a particular tests, or stated differently to the probability that an individual in which a given marker is absent will be correctly identified. A test which has "high specificity" has few, e.g., fewer than 1% false positive results, and thus rarely, if ever, gives an erroneous indication that a mutation is present, but may fail to detect the mutation in some or even many instances. Any marker that will reveal the presence of a tumor can be used. Markers are typically associated with alterations or mutations associated with the occurrence of a given tumor. Such mutations include, e.g., single or multiple basepair substitutions, single or multiple base pair insertions, and single or multiple basepair deletions. The marker set is selected so that it will be informative for a tumor of interest. When the tumor is colorectal cancer, a suitable marker set is one or more of the multi-target assay panel (MAP) described in Tagore et al., Clin. Colorectal Cancer 3:47-53, 2003, the contents of which are incorporated herein by reference in their entirety. The MAP includes specific mutations in the adenomatous polyposis coli (AFC), p53, and K-ras genes, a microsatellite instability marker 15 (BAT-26), and a marker of abnormal apoptosis (DNA Integrity Assay).

In general, the biological sample used in the second part of the method is any sample that is capable of containing, or is suspected of containing, tumor DNA. The source of the biological sample can be an organ, tissue or bodily fluid. A bodily fluid can include any fluid sampled from within the body, such as blood, a portion of blood such as plasma or serum, cerbrospinal fluids, or lymph, as well as local secretions, such as tears, semen, urine, sweat, sputum. A bodily fluid can also include a sample obtained by washing (e.g., bronchiolar lavage) or swabbing, including cervical smears, and the like.

Any cell or nucleic acid sample can be tested from a patient who has cancer or is suspected of having cancer. Suitable cell samples include, but are not limited to, tissue from a growth suspected or known to be cancerous, tissue adjacent to a resection of a tumor, and tissue distant from the site of a tumor, such as lymph nodes which are suspected of bearing metastatic cells. Cells or nucleic acids also can be obtained from bodily fluids or secretions, e.g., blood (including plasma or serum components of blood), urine, tears, sputum, saliva, or feces, which may contain cancerous cells or metastatic cells. Cell or nucleic acid samples also can be collected from other bodily secretions and tissues as is known in the art. A sample can be collected from suspected or known cancerous tissue or from bodily fluids or secretions harboring cancer cells as well as from suspected or known normal tissue or bodily fluids or secretions harboring normal cells. The effectiveness of therapy can be evaluated when a tumor has already been identified and found to contain a genetic mutation. Once a genetic mutation has been identified from the tumor of the patient, further tumor cells can be detected in tissue surrounding a resection or at other sites, if metastasis has occurred. Using the methods outlined above, the recurrence of the tumor or its incomplete removal can be assessed. Similarly, if a tumor has been treated using a non-surgical method such as chemotherapy or radiation, then the success of the therapy can be evaluated at later times by repeating the analysis. The step for determining the presence of a genetic mutation in a patient can be performed one or more times in order to monitor the development or regression of a tumor or to monitor the progress or lack of progress of therapy undertaken to eliminate the tumor. Monitoring can occur for any amount of time, including throughout a particular course of treatment, as long as the cancer is detectable, or for the rest of the life of the patient. In one embodiment, in the first step of the invention the identified mutation associated with the presence of cancer is selected from the group consisting of point mutations in the k-ras oncogene, point mutations in the APC gene, point mutations in the p53 gene, shortened forms of BAT-26 microsatellite, and DNA integrity assays. In the second step of the assay, one or more subsequent samples from the patient are screened for the presence of the above-mentioned mutations wherein the continued presence of the mutation indicates that the cancer continues to be present, and wherein the absence of the mutation means the cancer no longer continues to be present. As described herein, the treatment of an individual with a particular therapeutic can be monitored by determining the continued presence or absence of identified genetic mutations. The therapeutic regimen can then be maintained or adjusted (increased or decreased in dose). In a preferred embodiment, the effectiveness of treating a subject with an agent comprises the steps of; (i) obtaining a preadministration sample from a subject prior to administration of the agent; (ii) detecting the presence of a genetic mutation indicative of the presence of cancer in the preadministration sample; (iii) obtaining one or more post-administration samples from the subject; (iv) detecting the presence or absence of the genetic mutation in the post-administration sample; and (v) altering the administration of the agent to the subject accordingly.

In general, any assay can be used, provided that it is capable of detecting a marker associated with the disease in the body sample tested. Preferred assays are those that are sensitive enough to detect rare nucleic acids in a population of nucleic acid molecules. A suitable assay can be, e.g., allele-specific PCR (Rano et al., Nucl. Acids Res. 17:8392, 1989) or mutation amplification mismatch assay (MAMA). In the MAMA-PCR method, one of the two PCR primers, the 'mismatch detection' primer, has two mismatched bases at the Y end with respect to the wild-type sequence (ultimate and penultimate T base); but a single mismatch with the mutated allele (the penultimate 3' base). The two mismatched bases at-the 3' end of the primer, when annealed to the wild-type template, fail to amplify a PCR product. However, in the case of the mutant DNA, the primer anneals to the template and allows selective amplification and detection of the targeted clone. Cha et al., PCR Methods Appl. 2: 14-20, 1993; Glaab et al., Mutat. Res. 430: 1-12, 1993.

In other aspects of the invention, any of the embodiments described herein in the context of a tumor detection and/or monitoring assay may be used in conjunction with any of the other disease detection and/or monitoring assays described herein.

Unless otherwise defined, all technical and scientific terms used herein have the same meaning as commonly understood by one of ordinary skill in the art to which this invention belongs. Although methods and materials similar or equivalent to those described herein can be used in the practice or testing of the invention, suitable methods and materials are described below. All publications, patent applications, patents, and other references mentioned herein are incorporated by reference in their entirety. In the case of conflict, the present Specification, including definitions, will control. In addition, the materials, methods, and examples are illustrative only and not intended to be limiting. Other features and advantages of the invention will be apparent from the following detailed description and claims.

DETAILED DESCRIPTION OF THE INVENTION

Aspects of the invention relate to methods and compositions for detecting and/or monitoring diseases associated with one or more genetic abnormalities. In certain aspects, the invention provides methods for detecting indicia of a disease in a biological sample (e.g., the presence of one or more genetic abnormalities associated with an adenoma, a tumor, precancer, cancer, etc.). In some aspects, the invention provides methods for characterizing the genetic profile of diseased tissue (e.g., by determining the identity of one or more genetic abnormalities characteristic of the diseased tissue). In yet further aspects, the invention provides methods for monitoring the progress or recurrence of a disease associated with one or more identified genetic abnormalities in a patient.

In certain embodiments, indicia of disease (e.g., one or more genetic abnormalities including one or more point mutations, insertions, deletions, duplications, inversions, translocations, and/or other genetic abnormalities associated with the presence of disease) may be detected in a tissue biopsy (e.g., a biopsy of a polyp, tumor, or other growth) suspected of containing a high amount of abnormal cells or nucleic acid relative to normal cells and nucleic acid and/or ii) a heterogeneous biological sample (e.g., a sample derived from stool, blood, plasma, serum, sputum, or other biological secretion or bodily fluid) suspected of containing relatively few abnormal cells and/or nucleic acid (e.g., cell free DNA) amongst an abundance of normal cells and/or nucleic acid. It should be appreciated that relatively more abnormal nucleic acid (nucleic acid with one or more genetic abnormalities) will be present in a biopsy of tissue that is diseased than in a heterogeneous biological sample that does contain small amounts of disease-associated abnormal nucleic acid or cells. Therefore, detection assays with high sensitivity and specificity may be more important for the analysis of heterogeneous samples than for biopsy samples of diseased tissues. However, high sensitivity and high specificity assays also may be used for analyzing biopsy samples as the invention is not limited in this respect. High sensitivity detection assays, high specificity detection assays, high efficiency nucleic acid capture methods, nucleic acid stabilization methods, and other methods useful for isolating and/or detecting rare nucleic acids are described in more detail herein.

In some embodiments, an initial detection and/or characterization involves interrogating a plurality of genetic loci (e.g., disease associated markers) that may be present on a plurality of different target nucleic acids. For example, 5-10, 10-15, 15-20, 20-25, 25-30, or more different loci may be interrogated for the presence of any combination of mutations (e.g., point mutations, insertions, deletions, duplications, translocations, etc.) In certain embodiments, the initial assay interrogates genetic loci that have a sensitivity for detecting the disease (e.g., adenoma, cancer, precancer, tumor, etc.) in a subject of at least 50%, 75%, 80%, 85%, 90%, 95%, 98%, or 99%.

In certain embodiments, a genetic profile of diseased tissue in a patient may be identified based on the analysis of a biopsy sample and/or a heterogeneous biological sample. For example, the identity of one or more (e.g., 2, 3, 4, 5, 6, 7, 8, 9, 10, or more) specific genetic abnormalities (e.g., specific mutation(s) at one or more known loci) may be determined for a disease in a patient. In some embodiments, the presence of diseased tissue in a patient may be inferred from one or more analytical techniques described herein without the location of the diseased tissue being identified. In other embodiments, the location of diseased tissue may be known (e.g., identified as a physical growth such as a solid tumor, a polyp, an adenoma, or other growth). The location of diseased tissue may be determined based on a visual inspection (e.g., via colonoscopy) or an imaging technique such as a CAT, MRI, or other scan. In some embodiments, diseased tissue may be located after its presence is inferred from an analysis of a heterogeneous biological sample as described herein. Regardless of whether the location of diseased tissue is known, a genetic profile of the diseased tissue may be made (e.g., using one or more methods described herein). As explained above, higher sensitivity and specificity assays may be required to determine a genetic profile of abnormal nucleic acid in a heterogeneous biological sample than in a biopsy of diseased tissue.

Based on the knowledge of a genetic profile of a diseased tissue in a patient, the progression and/or recurrence of the diseased tissue may be monitored for that patient. In one embodiment, the presence and/or amount of the identified abnormal nucleic acid molecules is assayed in biological samples obtained from a patient at different time points in order to determine whether the amount of diseased tissue is increasing or decreasing in the patient. Based on the progression of the diseased tissue, certain therapeutic decisions may be recommended. The natural progression of a diseased tissue may be monitored according to aspects of the invention. Alternatively, the progression of the diseased tissue in response to a therapeutic treatment may be monitored. The therapeutic treatment may be a chemotherapeutic agent or other drug. In one embodiment, the progression of the diseased tissue may be monitored to determine whether the patient is responding to the treatment and whether a different treatment should be used. In another embodiment, the progression of the diseased tissue may be monitored to evaluate the effectiveness of a candidate drug. Accordingly, aspects of the invention may be used to screen one or more candidate drugs and/or evaluate their effectiveness and/or identify one or more therapeutically effective drugs (e.g., one or more anti-cancer or chemotherapeutic drugs). In certain embodiments, methods of the invention may be used to screen and/or identify drugs that are particularly effective for a disease associated with a particular genetic abnormality (e.g., a particular mutation, or a mutation in a particular gene or at a particular genetic locus, etc.) or a disease associated with a particular profile of two or more genetic abnormalities (e.g., particular mutations, or mutations in particular genes or genetic loci, etc.).

It should be understood that a disappearance or decrease in the amount of abnormal nucleic acid in a subsequent biological sample (relative to a reference level in a similar biological sample previously tested) is indicative of disease regression. In contrast, an increased amount or a reappearance of abnormal nucleic acid is indicative of growth or recurrence of diseased tissue (e.g., diseased cells). As discussed herein, due to the stochastic nature of certain isolation and analytical techniques particularly amplification techniques such as PCR) it may be necessary to use isolation, stabilization and/or capture methods that provide at least a threshold amount of genome equivalents of a target nucleic acid so that any measurement of the amount of abnormal nucleic acids is statistically significant. It should be appreciated that higher amounts of genome equivalents (a genome equivalent of a genetic locus is an amount of that locus that is present in a genome of the subject) of one or more predetermined genetic loci will provide more statistically significant and informative results.

In some embodiments, the presence of remaining diseased tissue (e.g., cells) following treatment (e.g., via chemotherapy, surgery, including colon resection, radiation, etc.) may be evaluated. In some embodiments, the recurrence of diseased tissue (e.g., cells) following a successful treatment (e.g., via chemotherapy, surgery, radiation, etc.) may be monitored. The monitoring may be performed at predetermined time intervals (e.g., monthly, bi-annually, annually, etc.) or when a patient schedules a medical appointment (e.g., at a doctor's office, clinic, hospital, etc.) or when a patient provides a sample to a diagnostic service for analysis. The presence of residual diseased cells or the recurrence of diseased cells after treatment would be an indicator for additional treatment (e.g., more of the same treatment or an alternative treatment).

It should be appreciated that time-dependent monitoring for the presence of diseased cells may be performed using different samples from those used in the initial detection and/or analysis step. For example, an initial analysis may be performed on a tissue biopsy whereas a subsequent follow-up may be performed on a heterogeneous biological sample (e.g., stool, blood, serum, plasma, sputum, urine, etc.). Similarly, monitoring may be performed using two or more different samples at any particular time point (e.g., stool and blood, serum, or plasma), or using different samples at different time points, or any combination thereof. In one embodiment, if an initial disease detection and/or analysis is performed on a particular heterogeneous biological sample, then subsequent monitoring may be performed on the same type of heterogeneous biological sample (e.g., stool, blood, plasma, serum).

It also should be appreciated that different types of detection assays may be used during monitoring and for initial disease detection and/or characterization. For example, an initial disease detection and/or characterization may be performed using an assay that screens for the presence of more than one genetic abnormality. In contrast, during subsequent monitoring, a method may be used that assays only for the presence of the particular genetic abnormality or abnormalities that were identified to be associated with diseased tissue in a patient. Accordingly, in certain embodiments, the monitoring stage assays for the progression or recurrence of diseased tissue based only on the particular genetic abnormalities that were originally identified to be associated with the diseased tissue. However, in other embodiments, monitoring assays also may involve screening for the presence of additional genetic abnormalities (e.g., the panel of mutations that were assayed for during the detection and/or characterization stage or a subset thereof or an additional or overlapping panel of mutations). Accordingly, aspects of the invention may be used to monitor for the presence of a second diseased tissue that is characterized by different genetic abnormalities. Alternatively, aspects of the invention may be used to monitor a changing profile of genetic abnormalities as a disease progresses (e.g., the accumulation of additional mutations). This information may be useful for prognostic purposes or to help determine appropriate therapeutic regimens based on the changing nature of the disease.

In one embodiment, an initial detection and characterization of a disease (e.g., adenoma, tumor, precancer, cancer, etc.) may be based on the presence of abnormal nucleic acids in a heterogeneous biological sample and the location of the diseased tissue may not be known. It should be appreciated that, according to the invention, heterogeneous biological samples may contain indicia of diseases that are remote to the tissue from which the sample was obtained. For example, stool may contain indicia of colon cancer. However, stool may contain indicia of other cancers (e.g., aero-digestive cancers or cancers in other tissues). Similarly, blood, plasma, or serum may contain indicia of a blood related cancer. However, they also may contain indicia of a cancer at any location in the body (e.g., colon, lung, liver, pancreas, stomach, esophagus, etc.). Similarly, other heterogeneous biological samples may contain indicia of cancer in one or more tissues or organs. In some embodiments, the location of diseased tissue in a patient may be identified once the existence of diseased tissue in the patient has been determined. However, in certain embodiments, the location of the diseased tissue may not be identified either by choice or because the disease is detected early and it is difficult to identify a physical growth or tumor associated with the disease. In other embodiments, the disease may be systemic and not located at one or more discrete positions in the body of the patient. Similarly, during the monitoring stages, heterogeneous biological samples may be assayed and the location of any detected disease may not be identified. In some embodiments, detection and/or monitoring may be used to detect the presence of metastasized cells at locations in the body remote from the site of the original diseased tissue.

It should be appreciated that the genetic profile of a disease such as cancer may be different in different patients. Accordingly, certain aspects of the invention relate to patient-specific detection and monitoring methods.

It also should be appreciated that the ability to detect and/or monitor early stage diseases (e.g., adenomas, precancerous growths, etc.) may be improved with the use of high specificity and sensitivity assays, high efficiency nucleic acid capture methods and devices, nucleic acid preservation methods and compositions, and/or other methods and compositions useful for the detection of rare abnormal nucleic molecules against a background of abundant normal nucleic acid molecules. In one embodiment, a high complexity and high sensitivity assay may be used for detection characterization. However, in other embodiments, a low complexity and high sensitivity or a low complexity and low sensitivity assay may be used depending on the scope of genetic abnormalities and are being assayed for and the type of tissue that is being analyzed (e.g., disease biopsy or heterogeneous biological sample). These and other methods are described in more detail herein.

In one aspect, methods are provided for detecting one or more particular mutations that are known to be associated with certain diseases or for detecting mutations at one or more genetic loci known to be associated with certain diseases. In certain embodiments, methods that can detect the presence of one or more mutations in particular target regions may be used. Useful methods include assays that can detect small amounts of mutant nucleic acid in a background of normal nucleic acid.

Certain aspects of the invention relate to combining single molecule sequence analysis technology (e.g., sequencing technology that was developed for whole genome sequence analysis) with specific sequence capture technology in order to detect rare genetic abnormalities at one or more genetic loci. Accordingly, aspects of the invention allow isolation and detection of very low frequency nucleic acid molecules having rare genetic abnormalities by combining i) a high efficiency specific sequence capture step that yields a nucleic acid preparation of relatively low genomic complexity containing several genome equivalents of a target nucleic acid of interest with ii) a high complexity analytical step, such as single molecule sequence analysis that can be used to characterize (e.g., sequence) each of a plurality of genome equivalents of the target nucleic acid. According to the invention, a high complexity analytical step may be used to detect (for example, with statistically significant confidence, e.g., greater than 90%, greater than 95%, or greater than 99% confidence) the presence or absence of a rare nucleic acid in a preparation of captured nucleic acid molecules having identical or substantially identical sequences.

Aspects of the invention relate to methods for detecting indicia of diseases (e.g., adenomas and/or early stage cancers) in biological samples. In particular, aspects of the invention relate to methods for detecting the presence of rare altered/mutant nucleic acid molecules that are present at a very low frequency in a biological sample containing a majority of normal nucleic acid molecules. According to the invention, altered/mutant nucleic acid indicative of adenoma and/or early stage cancer and/or other diseases may be present only at a frequency of less than 1% (e.g., less that 0.1%) of the total genome equivalents in a biological sample. Aspects of the invention are useful for both isolating and detecting such rare nucleic acid molecules. According to the invention, a detection assay may fail to detect nucleic acid molecules that are present at a very low frequency in a biological sample if either i) a capture step fails to capture a rare nucleic acid molecule that is present in a biological sample and/or ii) a detection reaction fails to detect a rare nucleic acid that is present in a preparation of captured nucleic acid.

According to aspects of the invention, the captured nucleic acid molecules may be relatively small, for example, from about 50 bases long to about several kilo-bases long (e.g., between about 100 bases and 10,000 bases, or about 150 bases, about 200 bases, about 250 bases, about 300 bases, about 350 bases, about 400 bases, about 450 bases, about 500 bases, about 1,000 bases, about 1,500 bases, about 2,000 bases, about 2,500 bases, about 3,000 bases, about 5,000 bases long, etc.). However, longer or shorter nucleic acid molecules may be captured. A typical biological sample may contain (or be processed to contain) nucleic acid fragments distributed across a range of sizes such as those described above. It should be noted that genomic nucleic acid in certain biological samples (e.g., stool samples) is already fragmented with typical fragment sizes ranging from 50 bases to several hundred bases long. A captured nucleic acid may be single stranded, double stranded, or contain both single and double-stranded regions. A captured nucleic acid may be DNA, RNA, or a modified form thereof.

It should be appreciated that aspects of the invention described herein, although particularly useful for the detection and/or characterization of adenomas or early stage cancer, also may detect later stage cancers. An assay with sufficient sensitivity to detect adenomas or early stage cancer will be sufficiently sensitive to detect altered/mutant nucleic acid from a later stage cancer that is present at a higher frequency in a heterogeneous biological sample. Similarly, aspects of the invention may be used to detect and monitor other diseases that are associated with the presence of abnormal nucleic acid in a biological sample. Aspects of the invention may be used to detect the presence, in a biological sample, of nucleic acid abnormalities associated with other diseases. Other diseases may include one or more inflammatory conditions, infections (including, for example, intracellular viral modifications), etc.

Detecting Rare Abnormal Nucleic Acid Molecules in Biological Samples:

Digital and/or High Complexity Sequence Analysis

Any of the assays described herein may be performed in a digital format wherein a sample is diluted into aliquots wherein each aliquot contains on average between 1 and 20 target nucleic acid molecules (e.g., DNA) for analysis (e.g., between 1 and 10 molecules, between 1 and 5 molecules, on average 1, etc.).

Aspects of the invention may include analyzing a predetermined number of genome equivalents of one or more target nucleic acids in order to determine whether one or more of the individual target nucleic acid molecules contains an abnormal sequence.

In aspects of the invention, the presence of a low frequency altered/mutant target nucleic acid molecule in a captured preparation of target nucleic acid molecules of low genomic complexity may be detected using a technique that was designed for analyzing nucleic acid samples of high genomic complexity. In some aspects of the invention, methods for sequencing whole genomes or substantial portions thereof (e.g., chromosomes or significant portions thereof) may be used to detect low frequency events in a nucleic acid sample of low genomic complexity.

High complexity analytical techniques may involve primer extension (e.g., single base extension or multiple base extension) or nucleic acid degradation techniques that can analyze large numbers of different template nucleic acid molecules (e.g., sequence or provide the identity of at least one nucleotide position in a template molecule). High complexity analytical techniques may involve the parallel and/or serial processing of a large number of different template nucleic acid molecules. High complexity analytical techniques may involve a parallel and/or serial analysis of single molecules (e.g., single nucleic acid molecule sequencing). In one aspect, a preparation of template molecules may be dispersed across a solid surface and individual molecules may be immobilized on the surface (e.g., a microscope slide or similar substrate).

A high sensitivity analytical technique may be used to characterize each immobilized molecule individually. For example, primer extension reactions may be used to incorporate labeled nucleotide(s) that can be individually detected in order to sequence individual molecules and/or determine the identity of at least one nucleotide position on individual template nucleic acid molecules. Detection may involve labeling one or more of the primers and or extension nucleotides with a detectable label (e.g., using fluorescent label(s), FRET label(s), enzymatic label(s), radio-label(s), etc.). Detection may involve imaging, for example using a high sensitivity camera and/or microscope (e.g., a super-cooled camera and/or microscope).

Accordingly, a "high complexity analytical step" may be a process that can analyze nucleic acid preparations of high genomic complexity. According to the invention, a preparation of target nucleic acid molecules of low genomic complexity such as those described herein may be used as template molecules and processed using a high complexity analytical technique. According to the invention, a high complexity analytical technique may be used to detect rare mutant/altered nucleic acid molecules in a preparation of many similar (or identical) nucleic acid templates of low genomic complexity.

Examples of high complexity nucleic acid analytical techniques are described herein. Additional analytical techniques are known in the art. Suitable techniques may be selected by one of ordinary skill in the art using the teachings of the invention. According to the invention, a sufficient number of target molecules should be captured and analyzed. A sufficient number is a number that provides a statistically significant result (e.g., a confidence level of at least 80%, at least 90%, at least 95%, or at least 99% that a particular alteration or mutation is either present or absent from a biological sample being analyzed).

In one embodiment, a digital analysis (e.g., a digital amplification and subsequent analysis) may be performed on at least a sufficient number of molecules to obtain a statistically significant result. Certain digital techniques are known in the art, see for example, U.S. Pat. No. 6,440,706 and U.S. Pat. No. 6,753,147, the entire contents of which are incorporated herein by reference. Similarly, an emulsion-based method for amplifying and/or sequencing individual nucleic acid molecules may be used (e.g., BEAMing technology).

In one embodiment, a sequencing method that can sequence single molecules in a biological sample may be used. Sequencing methods are known and being developed for high throughput (e.g., parallel) sequencing of complex genomes by sequencing a large number of single molecules (often having overlapping sequences) and compiling the information to obtain the sequence of an entire genome or a significant portion thereof. According to the invention, such methods, although designed for complex sequence analysis, may be particularly suited to sequence a large number of substantially identical molecules in order to identify the rare one(s) that contain a mutation or alteration.

High complexity analytical or sequencing techniques may involve high speed parallel molecular nucleic acid sequencing as described in PCT Application No. WO 01/16375, U.S. Application No. 60/151,580 and U.S. Published Application No. 20050014175, the entire contents of which are incorporated herein by reference. Other sequencing techniques are described in PCT Application No. WO 05/73410, PCT Application No. WO 05/54431, PCT Application No. WO 05/39389, PCT Application No. WO 05/03375, PCT Application No. WO 05/010145, PCT Application No. WO 04/069849, PCT Application No. WO 04/70005, PCT Application No. WO 04/69849, PCT Application No. WO 04/70007, and US Published Application No. 20050100932, the entire contents of which are incorporated herein by reference.

High complexity analytical or sequencing techniques may involve exposing a nucleic acid molecule to an oligonucleotide primer and a polymerase in the presence of a mixture of nucleotides. Changes in the fluorescence of individual nucleic acid molecules in response to polymerase activity may be detected and recorded. The specific labels attached to each nucleic acid and/or nucleotide may provide an emission spectrum allowing for the detection of sequence information for individual template nucleic acid molecules. In certain embodiments, a label is attached to the primer/template and a different label is attached to each type of nucleotide (e.g., A, T/U, C, or G). Each label emits a distinct signal which is distinguished from the other labels.

High complexity analytical or sequencing techniques may involve or be based on methods or technology described in Shendure et al., Nature Reviews/Genetics, Volume 5, May 2004, pages 335-344; Braslavsky et al., PNAS, Apr. 1, 2003, Volume 100, No. 7, pages 3960-3964; the entire disclosures of which are incorporated herein by reference.

In other embodiments, high complexity analytical or sequencing techniques may involve providing a primed target polynucleotide linked to a microfabricated synthesis channel, and flowing a first nucleotide through the synthesis channel under conditions such as to allow the first nucleotide to attach to the primer. The presence or absence of a signal is determined, the presence indicating that the first nucleotide was incorporated into the primer and the identity of the complementary base that served as a template in the target polynucleotide is determined. The signal is then removed or reduced and the process repeated with a second nucleotide. The second nucleotide can be either the same as the first nucleotide or a different nucleotide. The specific labels attached to each nucleic acid provide an emission spectra allowing for detection of sequence information of the nucleic acid molecule. In other embodiments, a plurality of different primed target polynucleotides linked to different synthesis channels is used. In further embodiments, the polynucleotide is attached to a surface. In some embodiments, a label is attached to the nucleotide.

In certain embodiments, a high complexity analytical or sequencing technique may be provided by Helicos BioSciences Corporation (Cambridge, Mass.). Briefly, in some embodiments, single strands of purified DNA with a universal priming sequence at each end of the strand may be generated. The strands are labeled with a fluorescent nucleotide and hybridized to primers immobilized on a surface. The primer duplexes are analyzed and the positions of each duplex recorded. DNA polymerase and a fluorescently labeled nucleotide are added and bind the appropriate primers. The sample is washed to remove unbound nucleotides and excess polymerase. The samples are analyzed and the positions of the incorporated nucleotides recorded. The fluorescent label is removed and a second labeled nucleotide is added and the process is repeated. The process may be repeated several times until a desired length is reached.

Other useful genome/complex sequencing methods include high throughput sequencing using the 454 Life Sciences Instrument System. Briefly, a sample of single stranded DNA is prepared and added to an excess of DNA capture beads which are then emulsified. Clonal amplification is performed to produce a sample of enriched DNA on the capture beads (the beads are enriched with millions of copies of a single clonal fragment). The DNA enriched beads are then transferred into PicoTiterPlate™ and enzyme beads and sequencing reagents are added. The samples are then analyzed and the sequence data recorded. Pyrophosphate and luciferin are examples of the labels that can be used to generate the signal.

A label may be, but is not limited to, a fluorophore, for example green fluorescent protein (GFP), a luminescent molecule, for example aequorin or europium chelates, fluorescein, rhodamine green, Oregon green, Texas red, naphthofluorescein, or derivatives thereof. In some embodiments, the polynucleotide is linked to a substrate. A substrate may be, but is not limited to, streptavidin-biotin, histidine-Ni, S-tag-S-protein, or glutathione-S-transferase (GST). In some embodiments, a substrate is pretreated to facilitate attachment of a polynucleotide to a surface, for example the substrate can be glass which is coated with a polyelectrolyte multilayer (PEM), or the polynucleotide is biotinylated and the PEM-coated surface is further coated with biotin and streptavidin.

In other embodiments, single molecule sequencing technology available from US Genomics, Woburn, Mass., may be used. For example, technology described, at least in part, in one or more of U.S. Pat. Nos. 6,790,671; 6,772,070; 6,762,059; 6,696,022; 6,403,311; 6,355,420; 6,263,286; and 6,210,896 may be used.

Other sequencing methods, including other high complexity analytical techniques also may be used to analyze DNA and/or RNA according to methods of the invention. It should be appreciated that a sequencing method does not have to be a single molecule sequencing method. In one embodiment, a method that sequences small numbers of molecules (e.g., 2, 3, 4, 5, 6, 7, 8, 9, 10, to about 15 or about 20 molecules) in a single reaction may be useful if the results can reliably detect the presence of a single (or a small number) of abnormal nucleic acids amongst the number of molecules that are being sequenced. It should be appreciated that the entire sequence of a captured target molecule does not need to be determined. It is sufficient to determine the sequence at a position, on the target molecule, suspected of containing an abnormality. It also should be appreciated that the analytical method does not need to identify the actual sequence of each molecule. In some embodiments, it may be sufficient to detect the presence of a small number (e.g., one or two) or a small percentage (e.g., 10%, 5%, 1%, 0.1%, 0.01% or lower) of abnormal molecules in a sample. For example, certain physical characterizations (e.g., mass detection such as mass spectrometry) may be used to distinguish normal from abnormal molecules and detect the presence of a small amount of abnormal nucleic acids associated with a disease.

Using Two or More Polymerases in Primer Extension Reactions

In certain aspects of invention, rare abnormal nucleic acids may be detected and/or characterized using primer extension reactions performed using two or more different polymerases for detecting and/or identifying mutant nucleic acids within a heterogeneous population of nucleic acids. In one embodiment, methods of the invention reduce misincorporation of terminator nucleotides (e.g., in single base-scanning reactions) by providing a first polymerase that preferentially incorporates extending nucleotides and a second polymerase that preferentially incorporates terminating nucleotides. In one embodiment, one or both of the polymerases misincorporate(s) an incorrect nucleotide (e.g., a terminating nucleotide) with a frequency of less than about 10%, for example less than about 5%, less than about 1%, or less than about 0.1%. It should be appreciated that misincorporation of a terminating nucleotide at a non-complementary position in an extension reaction can generate a false positive indication of the presence of a mutation at the site of misincorporation. According to the invention, a significant source of misincorporation may result from a correctly hybridized primer being extended with an incorrect nucleotide (i.e., a nucleotide that is not complementary to the template at the position where it is incorporated into the primer extension product).

In one aspect, misincorporation may be reduced by performing a primer extension reaction (e.g., a single base-scanning reaction) in the presence of at least two polymerases, each of which preferentially incorporates one of two nucleotides: an extending nucleotide or a terminating nucleotide. By including different polymerases for the extending and terminating nucleotides, polymerases that have low frequencies of incorrect base incorporation may be used. Preferably, one of the nucleotides is labeled and the other one is not labeled. The labeled nucleotide is preferably the one that is incorporated in the primer extension product when the template contains a sequence to be detected. In alternative embodiments, both first and second nucleotide may be labeled if they are differentially labeled such that the label on one of the nucleotides is detectably different from the label on the other nucleotide.

According to the invention, reducing the rate of misincorporation increases the sensitivity of primer extension assays (e.g., single base scanning assays) and allows for the detection of rare nucleic acid variations in heterogeneous biological samples. Misincorporation of a nucleotide corresponding to a mutation in a primer extension reaction can lead to a false positive detection of the presence of the mutation in a nucleic acid sample. In a typical primer extension reaction on a biological sample that contains mostly wild-type nucleic acids, misincorporation results in a background level of false positive signal that is high enough to obscure a true positive signal generated from a relatively small amount of mutant nucleic acids. Therefore, by reducing the amount of misincorporation, aspects of the invention provide highly sensitive and highly specific assays for detecting rare variant and/or mutant nucleic acid in heterogeneous biological samples.

In one aspect of the invention, single base scanning methods include identifying a target nucleic acid region suspected of containing a variation, and interrogating the target region using a single base scanning reaction. A primer is hybridized to a single stranded nucleic acid in the presence of extension nucleotides and polymerases, and the primer is extended through the target region creating primer extension products that are subsequently detected and/or quantified.

As discussed herein, different polymerases characterized by preferential nucleotide incorporation may be used to increase the signal to noise ratio for detecting low frequency events (e.g., mutant nucleic acids that are present at a low frequency in a biological sample containing an excess of non-mutant nucleic acids). In one embodiment, a first polymerase preferentially incorporates the extending nucleotide that is used, and a second polymerase preferentially incorporates the terminating nucleotide that is used. Preferential incorporation of one nucleotide over another can be measured using any suitable technique, for example by running parallel reactions which differ only in the type and concentration of each nucleotide. The relative incorporation efficiency of two different nucleotides can be reflected in the concentrations of nucleotides in the two reactions. For example, a first reaction that contains 10-fold more of a first nucleotide than a second reaction containing a second nucleotide demonstrates that insertion of the first nucleotide is 10-fold less efficient than that of the second nucleotide. These concentration levels can be measured by various methods, including, for example, performing titration assays, running the samples on DNA sequencing gels and visualizing the extent of nucleotide incorporation by autoradiography, running capillary electrophoresis assays and determining the levels of nucleotide incorporation. In one embodiment, if the incorporation of a first nucleotide over a second nucleotide is a 10-fold or greater difference, a determination can be made that the first terminator was preferentially incorporated. Preferably, a first polymerase incorporates a first nucleotide with between a 2 fold and a 100 fold preference. In certain embodiments, the ratio of incorporation may be between 5 fold and 50 fold, for example the ratio may be about 10 fold. However, ratios of less than 2 fold and greater than 100 fold can also be useful. The preference of the first polymerase for the first nucleotide relative to the second nucleotide can also be measured as a percentage increase in incorporation in an assay. Preferably, a first polymerase has between about a 5% and a 100% preference for a first type of nucleotide relative to a second type of nucleotide, for example between about 25% and about 75%. Examples of DNA polymerases with preferential nucleotide incorporation properties include those that preferentially incorporate dideoxy terminators over acyclic-terminators include Taq polymerase and Thermo Sequenase. (Gardner, A., (2002) "Acyclic and dideoxy terminator preferences denote divergent sugar recognition by archaeon and Taq DNA polymerases", Nucleic Acids Research, Vol. 30, No. 2 pp. 605-613.) Examples of DNA polymerases that preferentially incorporate acyclic terminators include Vent, Vent A488L, Deep Vent, 9° $N_m$, Pfu, and AcycloPol. In one embodiment of the invention, preferential incorporation can also be achieved by using dye-labeled terminators. Examples of DNA polymerases that preferentially incorporate dye-labeled terminators include Vent DNA polymerase, which preferentially incorporates dye-labeled dCTP analogs over unmodified dCTPs, and dye-acyCTPs over dye-ddCTPs, and Vent, Deep Vent, Pfu and 9° $N_m$ polymerases, which preferentially incorporate dye-acyNTPs over dye-ddNTPs. Similarly, preferential incorporation of terminator nucleotides relative to extending nucleotides or extending nucleotides relative to terminator nucleotides may be assessed and polymerases with preferential incorporation properties may be used as described herein.

Preferential Analysis and/or Characterization of Abnormal Nucleic Acids

Aspects of the invention may include a step that preferentially isolates abnormal nucleic acid molecules from a sample that includes both normal and abnormal nucleic acids. In one embodiment, PCR amplification can be performed in the presence of blocking oligonucleotides that suppress amplification of predetermined sequences in a population of nucleic acid sequences. The sequences whose amplification is blocked are typically those that are present in excess in a starting population of mixed nucleic acids. For example, if a sequence containing a mutation is present in a small amount in a population of nucleic acid sequences that do not contain the mutation, amplification of the latter sequences can be suppressed by adding blocking oligonucleotide or nucleotides prior to, or concurrently with, performing the PCR reaction. The blocking oligonucleotides preferably bind specifically (and in some embodiments, exclusively) to sequences not containing the mutation. The result is to increase the relative representation of the mutant sequence in a population of amplified sequences. A blocking oligonucleotide can be, e.g., a peptide nucleic acid (PNA), a locked nucleic acid (LNA), or a oligonucleotide including one or more phosphine analogues, PEGA modified antisense constructs 2'-O-methyl nucleic acids, 2'-fluoro nucleic acids, phosphorothioates, and metal phosphonates.

In one embodiment a DNA integrity assay (DIA) may be performed to detect the presence of long DNA fragments derived from abnormal cells (e.g., adenomas, cancerous or precancerous cells) that were shed into a lumen via a process that does not involve apoptosis. The DIA assay has been previously described in detail. The DIA assay involves detecting (e.g., in an amplification reaction such as a PCR reaction) the presence, in a biological sample from a lumen (e.g., a sample of stool, blood, plasma, serum, or other biological fluid described herein) of large DNA fragments (e.g., longer than about 200 bp, longer than about 500 bp, longer than about 1 kb, longer than about 1.5 kb, etc.) in an amount higher than expected (e.g., observed) for a healthy patient. In one embodiment, the amount of long DNA may be compared to a reference amount characteristic of a patient known to have a disease. More recently this assay has been converted to a real-time PCR methodology. In one embodiment, three unique PCR reactions (in duplicate) per loci may be run on I-Cycler instruments (BioRad; Hercules, Calif.). In one embodiment, a DIA method may involve capturing locus specific segments and performing small (e.g., ~100 bp) PCR amplifications remote from the capture site as an indicators of DNA length. DNA fragments for integrity analysis may be amplified at any locus, for example from four different loci: 17p13; 5q21; HRMT1L1; LOC91199 (named DIA-D, DIA-E, DIA-X, and DIA-Y, respectively). PCR primer sets and associated TaqMan probe for each locus of interest may be "walked" down the chromosome thereby interrogating for the presence and quantitation of increasing length of DNA of approximately, 100 bp, 1300 bp, 1800 bp and 2400 bp fragments of captured DNA. In one embodiment, purified DNA template (5 µl) was mixed with, 5 µl 10×PCR buffer (Takara), 10 µl dNTP's (2 mM) (Promega), 0.25 µl LATaq (5 U/µl; Takara), 24.75 µl molecular biology grade water (Sigma), 5 µl of a mix of PCR primers (5 µM; Midland) and TaqMan dual-labeled probes (2 µM; Biosearch Technologies). The I-Cycler was programmed as follows: 94° C. for 5 minutes, then 40 cycles of 94° C. for 1 minute, 55° C. for 1 minute, and 72° C. for 1 minute. Genomic standards, prepared as 20, 100, 500, 2500, and 12,500 GE/5 µl were prepared and used to generate a standard curve. In one embodiment, threshold Genome Equivalents (GE) values were determined for each of 12 PCR reactions (corresponding to the 1.3 kb, 1.8 kb, and 2.4 kb fragments across the 4 genomic loci) using a previously determined set of cancers and normals. In one embodiment, a positive result may require at least 4 of the 12 PCR reactions to be above individual PCR thresholds in order to prospectively determine cancers. However, in other embodiments, different thresholds may be used.

It should be appreciated that the presence of longer than expected DNA fragments may be indicative of the presence of diseased cells in a patient. However, the location of the disease is not necessarily tied to the nature of the sample that was analyzed. For example, the presence of prostate cancer, colon cancer (or other cancer) may be detected using DIA in plasma or serum (based on the presence of longer than expected free DNA molecules in the plasma or serum). Similarly, a positive DIA result on a stool sample may be indicative of a gastrointestinal disease (e.g., adenoma, cancer, precancer, tumor, inflammatory disorder, colon cancer, rectal cancer, etc.), but also may be indicative of an adenoma, cancer, precancer, or tumor in a different tissue or organ from which intact cells were shed and entered the gastrointestinal tract.

It also should be appreciated that long DNA is thought to originate from diseased cells. However, each long fragment of long DNA does not contain a genetic abnormality. Nonetheless, by interrogating one or more long DNA fragments (e.g., obtained using PCR primers separated by at least 200 bp, 500 bp, 1 kb, 1.5, kb or more) a sample may be enriched for nucleic acid sequences derived from diseased cells relative to normal cells. Accordingly, by interrogating a target nucleic acid (e.g., containing a region suspected of being abnormal in a diseased patient) of a length associated with abnormal cells, an increased signal to noise ratio of abnormal to normal may be obtained in an assay of the invention. Accordingly, interrogating longer DNA fragments may provide increased sensitivity for detecting rare abnormal (e.g., mutant) nucleic acids in a biological sample.

Sequence Scanning

In certain embodiments, the signal of mutant nucleic acid relative to normal nucleic acid may be enhance in a scanning reaction that interrogates a region for the presence of one or more mutations that may be associated with a diseased. In one aspect, current sequencing reactions may be modified such that only one terminator nucleotide (also referred to as a terminating nucleotide, i.e., a nucleotide that terminates an enzymatic primer extension reaction because it cannot be extended by a polymerase enzyme when it is incorporated into a primer extension product), and not all four terminator nucleotides, is provided in a primer extension reaction to allow for single base scanning, which is also referred to herein as single base tracking. The modified reaction is herein referred to as a single base tracking reaction. A single base tracking reaction of the invention may be used to detect the presence, in the nucleic acid region being scanned, of at least one aberrant nucleotide (e.g., a mutation, polymorphism, etc.) corresponding to the terminating nucleotide base being used in the scanning reaction. Aspects of the invention may be used to detect the presence of at least one variant nucleotide in at least one nucleic acid molecule being scanned even in the presence of an excess of nucleic acids that do not contain the variant nucleotide. Such an increased sensitivity has at least several uses. For example, methods according to the invention can be used to screen the human genome, providing for increased sensitivity for detection of low frequency genetic variations (e.g., when screening pools of nucleic acids obtained from a population of individuals in order to identify low frequency genetic variations). Methods according to the invention also can be used to interrogate one or more nucleic acid regions for the presence of at least one genetic variation (e.g., mutation) in at least one nucleic acid molecule in a biological sample that contains many nucleic acid molecules that do not have a genetic variation in the region being scanned. A nucleic acid region being scanned may be at least about 10 bases long, for example about 20 bases, about 50 bases, about 100 bases, about 150 bases, or about 200 bases long. However, in some embodiments the region may be shorter, longer, or of intermediate length.

Methods of the invention can be used to screen for mutations that are predictive or indicative of a disease state. The presence of a mutant nucleic acid molecule in a biological sample may be indicative of a disease such as cancer or pre-cancer (e.g., colon cancer or adenoma). Often, these mutations are present in a sample at a relatively low level, e.g., where the mutation is a somatic mutation in a nucleic acid population obtained from biopsied tissue. Methods according to the invention are more sensitive than current sequencing methods and can detect, in a scanning reaction, the presence of relatively low frequency mutations in a heterogeneous biological sample. According to aspects of the invention, an altered/mutant nucleic acid molecule originating from an adenoma and/or early stage cancer cell (or debris thereof) may be shed into a biological sample along with a large number of corresponding normal nucleic molecules that are shed from normal cells (i.e., non-adenoma and non-cancer cells) that line a lumen from which the biological sample originates or is obtained. An adenoma or early stage cancer is typically small and very few diseased cells (or debris thereof) are shed into the biological sample relative to normal cells (or debris thereof) from the normal tissue surrounding the adenoma or early stage cancer. As a result, altered/mutant nucleic acid molecules indicative of the adenoma or early stage cancer may be very rare relative to the corresponding normal nucleic acid molecules (i.e., nucleic acid molecules with an unaltered or non-mutant sequence from the same region of the genome as the altered/mutant nucleic acid molecule that has the altered/mutant sequence). According to aspects of the invention, indicia of certain later stage cancers also may be present at low frequencies in heterogeneous biological samples. Accordingly, aspects of the invention are useful for disease detection.

According to aspects of the invention, single base tracking reactions increase the sensitivity for detecting low frequency genetic events, at least because signals from bases at any one position in a sequence being scanned are no longer masked by signals from an alternate base in the wild type sequences present at higher concentrations in the sample. Sensitivity for low frequency mutations in a biological sample also may be increased by using certain ratios of extending nucleotides (nucleotides that can be extended in an enzymatic primer extension reaction) to terminating nucleotides; using two or more polymerases with different relative preferences for extending and terminating nucleotides; using certain analytical techniques (e.g., manual techniques, automated techniques, computer-implemented software, or any combination thereof) to quantify one or more signals associated with the incorporation of a known nucleotide (e.g., a labeled terminator nucleotide) at a known position in an extension reaction of the invention; or using any combination of the above techniques. Therefore, methods of the invention may be used to detect the presence of nucleotide sequences with altered residues when compared to a control "wild type" nucleotide sequence, where the nucleic acids with altered sequence make up about 50%, about 25%, about 10%, about 5%, about 4%, about 3%, about 2.5%, about 2%, about 1.5% or especially about 1% of the nucleic acids in the sample being analyzed, or even lower than 1%, for example about 0.5%, or about 0.1% or lower than 0.1% of the nucleic acids in the sample being analyzed.

In a preferred reaction, the terminator nucleotide is labeled. A preferred label is a fluorescent label, although it is within the skill of an artisan to use substitute labels of equal or higher sensitivity in signal detection, and/or equal or lower background signal noise. The DNA single base tracking reaction utilizes sensitive labeling techniques in order that the resulting sequence fragments may be analyzed and, e.g., compared to a known normal control sample to determine whether at least one genetic variation exists between the sample and normal control.

One aspect of the invention includes a method for detecting a difference between two nucleic acids. The method includes extending a first primer complementary to a target nucleic acid in the presence of a first nucleotide and a second nucleotide to produce at least one product. The first nucleotide is at least one deoxynucleotide, and more preferably is a mixture of four deoxynucleotides, namely dATP, dCTP, dGTP and dTTP ("dNTP mixture") used for the elongation step of the primer extension reaction. The second nucleotide is a terminator nucleotide, preferably includes a detectable label, and has the same base as one of the first deoxynucleotides. The method also includes detecting a signal from the at least one product and comparing the signal from the at least one product with a signal that is generated from a comparison nucleic acid in substantially the same manner as the signal is generated from the target nucleic acid. A difference between the signals indicates at least one difference between the target nucleic acid and the comparison nucleic acid. Signal differences include the addition of at least one peak, the deletion of at least one peak, or a shift in the position of at least one peak present in the sample as compared to the control.

In another aspect, a scanning reaction may be analyzed for signs of low frequency genetic events (e.g., one or more mutations) without using a comparison to a control or other reference nucleic acid of known sequence. For example, the presence of a mutation at a low frequency may be determined by quantifying the signals obtained for different positions of the primer extension product and determining whether one or more of the signals are present at a low, but statistically significant, level relative to signals for other positions (e.g., at about 10%, about 5%, about 1%, about 0.1% or lower than signals at other positions). Similarly, a corresponding loss of a small, but statistically significant, amount of signal (e.g., a loss of about 10%, about 5%, about 1%, about 0.1% or less than signals at other positions) at a position expected to generate a signal using a different terminator nucleotide may be indicative of (or confirm) the presence of a variant nucleotide at that position for a small number of nucleic acids in the sample being assayed.

The embodiments described above and below can have any or all of the following features. The method may include the step of amplifying a nucleic acid to form the target nucleic acid. The extending step can include extending the primer in the presence of the deoxynucleotides dATP, dCTP, dGTP, and dTTP. The target nucleic acid can be a nucleic acid suspected of containing a mutation. The target nucleotides to be screened in the methods of the invention may be genomic DNA, complementary DNA (cDNA), or RNA. Where the initial sample is RNA, it is preferred that the RNA is converted into DNA prior to further processing. The extending and comparing steps can be repeated. The extending and comparing steps can be conducted two or more times (e.g., at least four times) with the same primer, each time using a different one of adenine (A), cytosine (C), guanine (G) or thymidine (T) for the base of the second "terminating" nucleotide (i.e., each extension reaction contains only one type of extension terminating nucleotide, where the terminating nucleotide may be a dideoxynucleotide or an acyclonucleotide, and the base of the terminating nucleotide is chosen from A, C, G, or T).

A comparison nucleic acid can be a wild type nucleic acid. The signal from the comparison nucleic acid can be determined prior to, at the same time as, or after the signal from the target nucleic acid. The signal can include a fluorescent light emission. Alternatively, the signal results of the control sequence may be obtained from a database of nucleotide sequences. The comparison step may be done manually or by automation.

The methods described above or below can also have any or all of the following features. In certain embodiments, the method includes extending a second primer complementary to the target nucleic acid in the presence of the first nucleotide and the second nucleotide to produce at least one secondary product. In a preferred embodiment, the first nucleotide is a mixture of extending nucleotides (e.g., a deoxynucleotide (dNTP) mixture), the second nucleotide is a terminator nucleotide (dideoxynucleotide or acyclonucleotide) of only one base selected from A, C, G or T, and the at least one secondary product is the product of a primer extension reaction. The method may also include detecting a signal from the at least one secondary product and comparing the signal from the at least one secondary product with a signal that was generated from a comparison nucleic acid in substantially the same manner as the signal was generated from the target nucleic acid. A difference between the signals indicates at least one difference between the target nucleic acid and the comparison nucleic acid.

The methods described above or below may also include the following features. In one embodiment, a second primer complementary to a strand complementary to the target nucleic acid is extended in the presence of the first nucleotide and the second nucleotide to produce at least one secondary product. In a preferred embodiment, the first nucleotide is a mixture of extending nucleotides (e.g., a deoxynucleotide (dNTP) mixture), the second nucleotide is a terminator nucleotide (dideoxynucleotide or acyclonucleotide) of only one base selected from A, C, G or T, and the at least one secondary product is the product of a primer extension reaction. The method can then include detecting a signal from the at least one secondary product and comparing the signal from the at least one secondary product with a signal that is generated from a comparison nucleic acid in substantially the same manner as the signal is generated from the target nucleic acid. A difference between the signals indicates at least one difference between the target nucleic acid and the comparison nucleic acid.

In another aspect of the invention, a method for detecting a difference between two nucleic acids includes extending a first primer complementary to a target nucleic acid in the presence of a first nucleotide including a detectable label and a second nucleotide to produce at least one product. In a preferred embodiment, the first nucleotide is a mixture of extending nucleotides (e.g., a deoxynucleotide (dNTP) mixture), the second nucleotide is a terminator nucleotide (dideoxynucleotide or acyclonucleotide) of only one base selected from A, C, G or T, and the at least one product is the product of a primer extension reaction. The method also includes detecting a signal from the at least one product and comparing the signal from the at least one product with a signal that is generated from a comparison nucleic acid in substantially the same manner as the signal is generated from the target nucleic acid. A difference between the signals indicates at least one difference between the target nucleic acid and the comparison nucleic acid.

In another aspect of the invention, a method for detecting a difference between two nucleic acids includes extending a first primer including a detectable label and being complementary to a target nucleic acid in the presence of a first nucleotide and a second nucleotide to produce at least one product. In a preferred embodiment, the first nucleotide is a mixture of extending nucleotides (e.g., a deoxynucleotide (dNTP) mixture), the second nucleotide is a terminator nucleotide (dideoxynucleotide or acyclonucleotide) of only one base selected from A, C, G or T, and the at least one product is the product of a primer extension reaction. The method also includes detecting a signal from the at least one product and comparing the signal from the at least one product with a signal that was generated from a comparison nucleic acid in substantially the same manner as the signal was generated from the target nucleic acid. A difference between the signals indicates at least one difference between the target nucleic acid and the comparison nucleic acid.

In another aspect of the invention, a method for detecting a difference between two nucleic acids includes extending a first primer complementary to a target nucleic acid in the presence of a first nucleotide and a second nucleotide to produce at least one product. The second nucleotide is a terminator nucleotide and includes the same base as the first nucleotide. In a preferred embodiment, the first nucleotide is a mixture of extending nucleotides (e.g., a deoxynucleotide (dNTP) mixture), the second nucleotide is a terminator nucleotide (dideoxynucleotide or acyclonucleotide) of only one base selected from A, C, G or T, and the at least one product is the product of a primer extension reaction. The method also includes detecting a mass of the at least one product and comparing the mass of the at least one product with a mass that is generated from a comparison nucleic acid in substantially the same manner as the mass is generated from the target nucleic acid. A difference between the masses indicates at least one difference between the target nucleic acid and the comparison nucleic acid. Product masses may be determined using electrophoresis, mass spectrometry, or any other suitable technique as the invention is not limited in this respect.

For any of the assays described herein, a single base-tracking primer extension reaction may be cycled 2 or more times, for example between 5 and 40 times, about 30 times (e.g., 28, 29, 30, 31, or 32 times). For any of the assays described herein, PCR primers of between 20 and 50 nucleotides in length may be used. Similarly, primers used in single-base tracking extension reactions may be between about 20 and 50 nucleotides (e.g., about 30 or about 40) in length. However, other numbers of reaction cycles and primer lengths (e.g., longer, shorter, or intermediate lengths) may be used as the invention is not limited in this respect. It should be appreciated that the number of reaction cycles and primer lengths may be adapted to enhance the signal to noise ratio for detecting low frequency mutations in single-base scanning reactions described herein. However, it also should be appreciated that if a positive result is obtained using a single-base scanning reaction, the same assay may be repeated and/or a further assay may be performed in order to confirm the presence of a mutation and/or the frequency of the mutation in the biological sample. These and other aspects, along with advantages and features of the present invention herein disclosed, will become apparent through reference to the following description, the accompanying drawings, and the claims. Furthermore, it is to be understood that the features of various embodiments described herein are not mutually exclusive and can exist in various combinations and permutations. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and are not intended to be limiting. Other features and advantages of the invention will be apparent from the following detailed description and claims.

In one aspect, base-tracking reactions may be performed with a ratio of extending nucleotides to terminating nucleotides of about 50:1 (for example a ratio of about 12.5:1 for each individual extending nucleotide to the terminating nucleotide). However, lower ratios may be used provided that the rate of misincorporation of the labeled nucleotide does not exceed the level of mutant nucleic acid that is being assayed for. Ratios of extending nucleotides to terminating nucleotides may be between about 10:1 and about 100:1 (e.g., about 10:1, 20:1, 30:1, 40:1, 50:1, 60:1, 70:1, 80:1, 90:1, or an intermediate value). However, other ratios may be used as the invention is not limited in this respect. Typically, a ratio of extending nucleotides to terminating nucleotides may be lower than one used in a standard sequencing reaction but higher than one used in a standard primer extension reaction (e.g., single base extension reaction) designed to detect a specific mutation. A ratio may be chosen so that the single base-scanning reaction extend for between about 20 to about 150 bases, for example for between about 50 and about 100 bases so that any low frequency genetic event produces sufficient signal to be detected and/or quantified.

The products of the single base tracking reactions (e.g., from each amplification fragment) may be separated using electrophoresis, e.g., CAGE (capillary gel electrophoresis). The shorter fragments elute from the gel first while the longer fragments elute from the gel last. As the fragments are eluted from the gel, the signal from the label is detected and a pattern of signals for all the fragments is determined (examples of patterns are shown in the Examples below). For example, if fluorescent labels are used, an ABI 3100 DNA Sequencer can be used to read out the signal pattern. Each reaction can be analyzed independently and/or multiplexed.

In one embodiment, the same single base tracking procedure may be carried out for a known normal nucleic acid sequence (e.g., a wild type sequence). The signal pattern generated for the normal sequence may be compared with the signal pattern from the sample. Insertions, deletions and point mutations may be identified by a change in the peak pattern relative to the wild type peak pattern. This comparison can be undertaken manually or in an automated fashion. For example, comparisons may be performed using software that quantifies the amount of different types of signals at different positions (e.g., for extension products of different lengths). The amount of a signal at a position that is not expected to have a signal in a wild-type template may be used to determine a frequency of mutant or variant nucleic acids in a biological sample. This modified sequence reaction produces results that can detect a mutant to wild type ratio in a sample of less than 1:1. For example, the invention can detect mutations present at a ratio of about 1:4 (mutant to wild type), about 1:10 (mutant to wild type), about 1:100 (mutant to wild type), or less than about 1:100 (mutant to wild type), for example about 1:1,000 or less. Accordingly, this tracking method has a higher sensitivity for mutations than do current sequencing reactions.

Additionally, the single base tracking reactions described herein can be run in the forward and reverse directions. For example, if the procedure described above was the "forward" direction, primers would be designed to sequence the amplification fragments in the opposite direction. This reverse direction single base tracking is a manner to confirm that the result obtained in the forward direction is accurate. The single base tracking reaction can be run in the forward and/or reverse directions as many times as is desired to confirm the results.

In a first step, an embodiment of the invention may include preparing a nucleic acid sample (typically DNA) for scanning. In some embodiments, a nucleic acid preparation may be amplified from a biological sample. To the extent enough nucleic acid exists in the sample, amplification is not required. However, to the extent amplification is desired, any of a variety of methods can be used including, but not limited to PCR, RT-PCR, OLA, rolling circle, single base extension, and others such methods known to one skilled in the art. To the extent PCR is used, primers are designed to amplify a targeted region of a genome or other source of nucleic acid. For example, the region may be a mutation cluster region ("MCR") or any other region suspected of being associated with a mutation diagnostic for a disease (e.g., mutations present in a gene such as APC, p53, BAT-26, PIK3 CA, beta-catenin, or a portion thereof such as exon 9 or exon 20 of the PIK3CA locus, exon 5 of the beta-catenin locus, or a portion of any of the above suspected of containing a mutation). Nucleic acid regions that may contain one or more nucleic acid mutations associated with cancer are described for example in Cancer Research (Mar. 15, 1998) 58, pp 1130-1134, and Science (Apr. 23, 2004) 304(5670): 554, the disclosures of which are incorporated herein in their entirety. However, aspects of the invention may be useful for scanning any genomic region in which one or more mutations may be associated with diseases such as cancer (e.g., a "hotspot" region for mutations associated with diseases such as cancer). If using PCR, a primer pair may be designed to amplify the entire region in one reaction. Alternatively, several primers can be designed to overlap. In this case, two or more sets of primers are used to amplify the region. The sets of primers can be used in separate amplification reactions or in one multiplex reaction.

One of the PCR primers that generates each fragment may be biotinylated if post-PCR cleanup is desired. For example, the biotinylated PCR amplification fragments can be run over a column having complementary streptavidin bound to beads. This removes the amplified fragments from the rest of the nucleic acid in the amplification reactions, simplifying the ability to see relatively low amounts of mutant nucleic acid. The bound amplification fragments are then optionally eluted from the column. Alternatively, other binding partners that are known in the art may be used with one of the partners attached to the PCR primer. Attachment may be by any suitable linkage or linkage method known to one skilled in the art.

Target Molecules:

It should be appreciated that in order to determine with statistical significance whether an abnormal nucleic acid is present in, or absent from, a biological sample, a minimum or threshold number of genome equivalents of a target nucleic acid need to be characterized (e.g., sequenced in whole or in part) to determine if any one of them is abnormal. For suspected rarer abnormalities, higher numbers of genome equivalents need to be characterized to reach a statistically significant conclusion that the sample does or does not contain the abnormality. For example, if a mutation is suspected to be present in 1% (if at all) of the copies of a target nucleic acid in a sample, then 100 or more copies (genome equivalents) of the region suspected to be mutant should be characterized. In this embodiment, the result has higher statistical significance if about 200; 300; 400; 500; 600; 700; 800; 900; 1,000 or more target nucleic acid molecules are sequenced. In one aspect, a statistically significant result may be obtained for an abnormality suspected to be present in x % of the target nucleic acids in a biological sample (or in x % of the captured nucleic acid molecules) if 100/x or more genome equivalents of a target nucleic acid containing the region suspected of being abnormal are characterized. In certain embodiments, about 200/x; about 300/x; about 400/x; about 500/x; about 600/x; about 700/x; about 800/x; about 900/x; about 1,000/x; about 5,000/x; about 10,000/x; about 50,000/x; about 100,000/x; about 500,000/x; about 1,000,000/x or more genome equivalents are isolated, captured, analyzed, and/or characterized. For example, if a 0.1% level of abnormality is suspected, 1,000 or more genome equivalents should be characterized. Similarly, for a 0.01% level, 10,000 or more genome equivalents should be characterized. Accordingly, appropriate sample volumes and isolation steps should be used to provide sufficient genome equivalents for subsequent analysis. It should be appreciated that less than 100/x genome equivalents may be used under certain circumstances where statistical significance is less important.

In certain embodiments, two or more markers may be analyzed in a single assay. Accordingly, two or more different target nucleic acid regions may be isolated. In one embodiment, the number of genome equivalents of each target molecule is above a threshold number sufficient for a statistically significant result to be obtained upon subsequent sequence analysis of the captured molecules or a portion thereof. In general, the threshold level would be set at the same level for each different abnormality being assayed for in a biological sample.

It should be appreciated that the level of sensitivity (e.g., how low a percentage of abnormality can be detected) may determine the earliest stage at which the presence (e.g., recurrence) or absence of a disease may be detected with statistical significance. For example, if a predetermined threshold level of at least 10,000 genome equivalents are characterized, a 0.01% level of mutation may be detected with statistical significance. Detecting a mutation at a 0.01% level allows a disease to be detected earlier than using a 0.1%, 1%, 10% detection level, because the 0.01% level corresponds to a stage in the disease when the diseased cells have not multiplied to a level that would allow them to be detected using a 0.1%, 1%, or 10% detection threshold. Similarly, a 0.1% threshold allows earlier detection than a 1% threshold (and 1% earlier than 10% etc.). Characterizing hundreds or thousands of (e.g., 5,000; 10,000; 50,000; 100,000 or more) copies of a single genetic region or of each of several genetic regions may seem like a large amount of work. However, high complexity analytical methods such as those developed for genome sequencing (and particularly those developed for single molecule sequencing) can be used for this task since they are capable of sequencing many more molecules than required for statistical significance according to the invention. For example, the number of single molecules required for sequencing an entire genome, or even a significant portion of a genome, is greater than the number of single molecules that may be sequenced for statistical significance according to certain aspects of the invention. A particular feature of methods of the invention is that the single molecules being sequenced have similar, identical, or overlapping sequences, because they were isolated as multiple genome equivalents including a locus of interest. This differs from genome sequencing where most of the single molecules being sequenced have different sequences since they are generated to represent different portions of the genome. Accordingly, while methods of the invention use high-complexity analytical techniques, these techniques may be adapted for the particular configurations required by aspects of the invention. For example, a predetermined genetic locus may be analyzed using a single sequencing primer that is expected to work on all of the isolated target molecules. This primer may be sequence specific and contain at least about 10, 15, 20, 25, 30, 35, 40, 45, 50, or more nucleotides that are complementary to a region of the target molecule in proximity with the region suspected of containing an abnormality. In some embodiments, two or more different primers (e.g., 3, 4, 5, 6, 7, 8, 9, 10, etc.) may be used in different sequencing reactions (for example, each using a threshold number of genome equivalents of target nucleic acid) to provide further confidence in the sequencing results. In contrast, certain genome sequencing methods involve a plurality of different primers in a single analysis so that each primer can hybridize to, and provide sequence information for, a different part of the genome. Similarly, data or sequence analysis techniques of the invention may be adapted for comparing many copies of a similar, identical, or overlapping sequence in order to determine if one or more of the molecules being characterized (e.g., sequenced) contains a genetic abnormality of interest. It should be appreciated that a genetic abnormality may be any form of mutation (for example, a point mutation, a transition, a transversion, a duplication, a deletion, an inversion, a translocation, or any other form of mutation). In certain aspects of the invention, analytical methods also may be adapted to detect rare modified nucleic acids such as hyper- or hypomethylated nucleic acids that may be associated with a disease.

Aspects of the invention may involve using a high number of amplification cycles to reach a point at which amplification is saturated in order increase the probability of amplifying any mutant templates that are present in a sample. For example, the number of amplification reactions may be above 30, for example above 40, above 50, about 60 or above. In one embodiment, an entire amplification product may be analyzed (e.g., in one single base scanning reaction). In other embodiments, an entire amplification reaction may be partitioned into aliquots that are analyzed using two or more different assays (e.g., single base scanning reactions), optionally with two or more primers.

However, in some embodiments, due to the stochastic nature of nucleic acid recovery in typical sample preparations and the stochastic nature of nucleic acid amplification reactions, the presence of one or a small number of abnormal nucleic acids may not be detected even if a large number of amplification cycles are used. For example, normal nucleic acids may be "preferentially" amplified in the first few rounds of an amplification reaction even if abnormal nucleic acids are present in the sample. This may occur due to the stochastic nature of the amplification reaction (for example, not all templates are amplified in each cycle) and the presence of only very small numbers of abnormal nucleic acid molecules in the biological sample. This "preferential" amplification of normal nucleic acid molecules in the first few cycles may result in an over-representation of the normal nucleic acid in the final amplified product (and therefore a lower percentage of abnormal nucleic acid in the final amplified product than in the initial biological sample). Therefore, in one aspect, methods of the invention may include a high yield or high efficiency nucleic acid preparation and/or capture procedure in order to isolate as much abnormal nucleic acid as possible from a biological sample.

High Efficiency Isolation of Target Molecules

Any method that is suitable for isolating a threshold number of genome equivalents of one or more target molecules may be used in certain aspects of the invention. In preferred embodiments, a specific hybrid capture method may be used. A hybrid capture method may involve using a capture probe to bind to a target nucleic acid. The bound product then may be isolated. In one embodiment, a capture probe may be bound to a solid surface thereby acting as an anchor for isolating a target molecule. In other embodiments, a capture probe may be modified in a manner that allows it to be isolated or purified from a sample. For example, a capture probe may biotinylated, attached to an antigen, attached to a magnetic particle, attached to a molecular weight marker, attached to a charged particle, attached to another particle or other molecular "hook" that can be used to isolate that capture probe and thereby isolate a target molecule that is hybridized to the probe. In some embodiments, a capture probe binds to (and captures) a target molecule at a region near a region suspected of containing an abnormal sequence. Accordingly, a capture probe may bind to a normal sequence and capture target molecules with or without a genetic abnormality. However, in some embodiments a capture probe may be specific for a predetermined mutation and preferentially bind to target nucleic acids containing the mutation.

In aspects of the invention, a nucleic acid preparation is captured by repeated exposure of a biological sample (for example, a processed biological sample) to a capture probe on a solid support or in a medium, for example, by the rapid flow of the sample past a capture probe for the target nucleic acid molecule. The repetitive nature of such a method allows for a target molecule to bind and enhances the total number of molecules bound to the capture probe, providing a high yield capture. The solid support may be an electrophoretic medium (e.g., gel or beads) and the repetitive exposure of the sample to the capture probe may involve exposure to repeated cycles of electrophoresis in alternate directions (back and forth across a solid support region containing one or more different types of capture probe). In some aspects, a sample is added to a portion of an electrophoretic medium having at least two regions arranged consecutively in a first spatial dimension. In some aspects, at least one of the at least two regions includes a first capture probe which is immobilized within that region. An electric field is applied to the electrophoretic medium in a first direction which is parallel to the first dimension. An electric field is then applied to the electrophoretic medium in a second direction which is opposite to the first direction. In further aspects, the electric field is applied repeatedly in each direction. For further details see for example U.S. Application No. 60/517,623 and U.S. application Ser. No. 10/982,733, the entire contents of which are incorporated herein by reference.

In aspects of the invention, a sample may be exposed repeatedly to a capture probe using chromatographic methods, for example high performance liquid chromatography (HPLC), fast performance liquid chromatography (FPLC), etc.

In some embodiments, the captured sample may be amplified using PCR (or other amplification technique) to obtain a pool of DNA of an expected size. However, amplification is not required as the invention is not limited in this respect.

In some aspects of the invention, a capture probe may be any molecule capable of binding a target molecule (or a non-target molecule as described below). According to the invention, a target molecule is a molecule that contains a region suspected of being altered or mutant in disease (e.g., in adenomas or early stage cancers). Accordingly, a capture probe binds to a portion of a nucleic acid that is adjacent to (or overlaps) a position or region suspected of being mutant or altered. The capture probe should bind sufficiently close to the suspected position or region to effectively capture a significant number of target molecules that contain the suspected position or region. For example, in one embodiment the capture probe should bind to a portion of a nucleic acid that is within 5,000 bases (e.g., within 2,500 bases, within 1,000 bases, within 750 bases, within 500 bases, within 250 bases, or within 100 bases) of the position or region suspected of being mutated or altered. A capture probe may be between about 30 and about 40 bases long (e.g., about 31, 32, 33, 34, 35, 36, 37, 38, or 39 bases long). However, shorter or longer capture probes may be used. In some aspects, a capture probe selectively binds to a target molecule in a sample. In one embodiment, a capture probe is outside of a region of the nucleic acid to be amplified. It should be appreciated that a capture probe may bind to target nucleic acid molecules with overlapping sequences, because nucleic acid fragmentation (e.g., resulting from natural fragmentation or exposure to a fragmentation technique) typically generates overlapping fragments of different sizes.

According to aspects of the invention, the capture probe can bind a target molecule during electrophoresis under appropriate conditions, such as pH, temperature, solvent, ionic strength, electric field strength etc. One of ordinary skill in the art would be able to adjust any condition as required to achieve optimal binding. A capture probe may include, but is not limited to, one or more peptides, proteins, nucleic acids, amino acids, nucleosides, antibodies, antibody fragments, antibody ligands, aptamers, peptide nucleic acids, small organic molecules, lipids, hormones, drugs, enzymes, enzyme substrates, enzyme inhibitors, coenzymes, inorganic molecules, polysaccharides, and/or monosaccharides.

When a nucleic acid capture probe is used (e.g., an oligonucleotide, a DNA, an RNA, a PNA, or other form of natural, synthetic, or modified nucleic acid) it should have a sequence that is sufficiently complementary to a portion of the target nucleic acid to bind specifically to the target nucleic acid under the conditions used for capture. In some embodiments, the capture probe may have a sequence that is 100% complementary. However, in other embodiments, the sequence may contain a few non-complementary nucleotides (e.g., at the 3' or 5' end). It should be appreciated that a small number of non-complementary nucleotides may be non-complementary. For example, the capture probe may be between 80% and 100% complementary (e.g., about 85%, about 90%, or about 95% complementary) to a portion of the target nucleic acid. However, other degrees of complementarity may be used provided that the capture probes can capture a sufficient number of genome equivalents of a target nucleic acid with sufficient specificity for subsequent analysis. It should be appreciated that aspects of the invention do not require a pure sample of target nucleic acids. Nucleic acids other than the target nucleic acids may be isolated and included in the analytical step provided that they do not interfere with the sequence analysis in a way that would reduce the significance of the results to a level that falls below a predetermined level of statistical significance.

In embodiments of the invention, exposure of a biological sample (for example a crude preparation of total nucleic acid from a biological sample) to immobilized capture probe(s) may be repeated between 2 and 100 times, e.g., between about 5 and about 50 times, between about 10 and about 40 times, or about 11, 12, 13, 14, 15, 16, 17, 18, 19, 20, etc. times, including about 25, 30, or 35 times.

A captured preparation of target nucleic acid molecules (e.g., of low genomic complexity) may be eluted using any suitable technique and prepared (e.g., single stranded molecules may be prepared) for subsequent analysis using a technique for analyzing nucleic acid samples of high genomic complexity. Sample capture techniques described herein may be used to analyze DNA and/or RNA.

Biological Samples:

In certain embodiments of the invention, a sample may be prepared from a specimen selected from the group consisting of stool (including stool homogenate), sputum, pus, blood (including whole blood, blood plasma, and blood serum), urine, cerebrospinal fluid, seminal fluid, saliva, breast nipple aspirate, biopsy tissue, cerebrospinal fluid, and pancreatic fluid. In aspects of the invention, a sample may be a biological sample. A biological sample may be, but is not limited to, stool, whole blood, serum, plasma, tears, saliva, nasal fluid, sputum, ear fluid, genital fluid, breast fluid, milk, colostrum, placental fluid, amniotic fluid, perspirate, synovial fluid, ascites fluid, cerebrospinal fluid, bile, gastric fluid, aqueous humor, vitreous humor, gastrointestinal fluid, exudate, transudate, pleural fluid, pericardial fluid, semen, upper airway fluid, peritoneal fluid, fluid harvested from a site of an immune response, fluid harvested from a pooled collection site, bronchial lavage, urine, biopsy material, a nucleated cell sample, a fluid associated with a mucosal surface, hair, or skin. A sample also may be a pooled sample containing biological material and or isolated nucleic acids from a plurality of subjects (e.g., 2, 3, 4, 5, about 10, or more). However, any tissue or body fluid specimen may be used according to methods of the invention (e.g., either directly as a crude sample or as a source of a processed sample) for nucleic acid isolation and/or characterization.

Aspects of the invention relate to methods for detecting the presence of one or more mutations in a region of a mutant nucleic acid that may be present in a biological sample at a low frequency (e.g., about 10%, 5%, 1%, 0.1% or lower) relative to corresponding normal (non-mutant) nucleic acid. Aspects of the invention are useful for detecting low frequency mutations that may occur at one or more positions within a region suspected of being altered (e.g., containing one or more mutations). Such a region may be a mutation hot spot of between 50 bases and 1,000 based in length. For example, a region suspected of containing one or more mutations may be about 100 bases, about 200 bases, about 300 bases, about 400 bases, about 500 bases, about 600 bases, about 700 bases, about 800 bases, or about 900 bases long. However, shorter, longer, or intermediate length regions may be assayed. According to the invention, the presence of one or more mutations in such a region may be difficult to detect using known methods, because mutant nucleic acid molecules may be present at a low frequency in a nucleic acid preparation and also because the position of the one or more mutations within such a mutant nucleic acid region may not be known. Aspects of the invention may involve performing single base scanning sequencing reactions under conditions that enhance the signal obtained from a mutation within a specific region. For example, mutant signal may be enhanced by increasing the amount of template that is introduced, using a ratio of terminator to extending nucleotides that increases the signal of low frequency events, running relatively short sequencing reactions (e.g., about 100 bases) to increase the signal, using two enzymes with different specificities for terminating and extending nucleotides to reduce the amount of misincorporation that may result in a false positive, performing analysis using appropriate software to quantify the amount of signal (e.g., area under the curve) for each base and quantify the amount of mutant material, or any combination thereof.

In aspects of the invention, an increase in sensitivity may be achieved by using large amounts of sample. In embodiments of the invention, a large amount of sample may be processed in order to increase the confidence level of isolating or capturing a rare event indicative of very early stage disease (e.g., an adenoma, an early stage cancer, recurrence, etc.). In some embodiments, large volumes of sample may be processed in order to obtain sufficient genome equivalents of one or more target nucleic acids of interest (e.g., target nucleic acids that are being screened for the presence of a mutation, or target nucleic acid(s) that are being monitored for the progression or recurrence of a genetic abnormality that has been associated with a disease in a patient). For example, about 5 g, about 10 g, about 15 g, about 20 g, about 25 g, about 30 g, about 35 g, about 40 g, about 45 g, about 50 g, about 55 g, about 60 g, about 65 g, about 70 g, about 75 g, about 80 g, about 85 g, about 90 g, about 95 g, about 100 g, about 150 g, about 200 g, or more sample (e.g., stool sample) may be processed using a capture technique described herein. For example, more than about 5 mls, about 10 mls, about 15 mls, about 20 mls, about 25 mls, about 50 mls, about 75 mls, about 100 mls, about 200 mls, about 300 mls, about 400 mls, about 500 mls, or more blood may be analyzed or processed to isolate plasma or serum for subsequent analysis. Intermediate volume ranges between any of the specific volumes set forth above also may be used.

In one embodiment, aspect of the invention involve screening isolated nucleic acids for mutations and/or integrity. The isolated nucleic acids may be cell free and may be isolated from tissues, blood, serum or plasma. In one embodiment, an important step in the isolation of cell-free nucleic acids from a biological fluid sample (e.g., blood) may be a filtration step. For example, the filtration may involve passing a sample of bodily fluid (e.g., blood) through a filter that excludes cells but not free nucleic acids (e.g., a 0.45 micron filter or smaller).

Nucleic Acid Preservation:

Methods for Stabilizing Nucleic Acids in Biological Samples

According to aspects of the invention, stabilization solutions may be particularly useful for preserving nucleic acids to detect one or more indicia of disease and/or to monitor disease progression, regression or recurrence.

In certain embodiments, high sensitivity may be achieved by preserving nucleic acid integrity in biological samples (e.g., the integrity of free DNA in blood, plasma, or serum, or DNA in stool). It has been unexpectedly found that an abnormal DNA molecule can be stabilized and/or enhanced by mixing, or incubating, a patient sample known to or suspected of containing DNA indicative of a disease with a stabilization solution prior to performing a DNA integrity assay or other nucleic acid assay described herein. The stabilization solution typically includes one or more buffers, and/or chelating agents, and/or salts. Aspects of the invention are particularly useful for nucleic acid integrity assays. However, mutation detection (for example, in a multiple mutation assay) and hypermethylation analysis also can benefit from aspects of the invention.

According to the invention, an important challenge for cancer (e.g., colon cancer) detection from stool is to preserve the integrity of human DNA in the hostile stool environment, in order to recover, amplify, and interrogate the DNA for known cancer related abnormalities. Nucleases that are active in stool have the potential to rapidly degrade DNA, including the minor human DNA component, and measures may be taken to minimize their negative impact. Typically, clinical samples are frozen as quickly as possible after collection. However, in order to use fecal DNA tests in population screens, it should be expected that there will be some variability in the time between sample collection and shipping to testing labs, and furthermore, some variability in the temperature at which stool samples are transported. In order to eliminate any variables in sample handling that might have an impact on assay performance we have run controlled sample incubation experiments and looked at how different markers in a multi-target assay are affected.

Markers may be chosen that yield an acceptable clinical sensitivity for the intended application such as screening a population for indicia of a disease. In addition, for stool sample analysis, mutation detection methods should offer sufficient analytical sensitivity since the human DNA recovered from stool is highly heterogeneous. Normal cells are sloughed into the colonic lumen along with the mutant cells. Therefore, in one embodiment, analytical methods should detect as little as 1% (or less) mutant DNA in the presence of excess wild-type DNA. Also, certain sample preparation methodologies may be used for maximum recovery of human DNA from samples. The vast majority of DNA recovered from stool often is bacterial in origin, with the human DNA component representing only a small minority. Certain purification methodologies can efficiently select for the rare human component, and since the mutant copies (when they exist) represent only a small percentage of the total human DNA from stool it may be important to maximize the recovery of human DNA in order to maximize the probability of amplifying mutant copies in the PCR reactions. In one embodiment, gel electrophoresis methods for capturing human DNA may be used. However, according to the invention, it may be particularly important to preserve sample DNA for purification, especially when looking for early indicia of diseases (e.g., indicia of adenomas or early stage cancers that may be present in less than about 1%, or about 0.1% or less of human genomes isolated from a stool sample). A common method to insure that DNA remains stable is to freeze stool samples as quickly as possible after collection, or to receive samples in centralized testing labs as quickly as possible. However, in order to provide the option of decentralized sample analysis and still retain maximum sample integrity, it is desirable to use a more robust and standardized sample handling method. Similar considerations may apply for handling certain blood samples, plasma samples, serum samples, or other biological samples.

In one aspect, the invention provides methods for stabilizing biological samples (e.g., stool samples, blood samples, plasma samples, serum samples, etc.) by adding a stabilization solution to a sample as soon as possible after the sample is obtained. Methods of the invention do not require refrigeration or freezing. Aspects of the invention are based, in part, on the surprising discovery that nucleic acids in certain biological samples are stable at room temperature for hours, and even days (e.g., 1 day, 2 days, 3 days, or longer). However, in certain embodiments, samples with stabilization solution may be refrigerated or frozen. Aspects of the invention are particularly useful for preserving samples for nucleic acid integrity analysis. However, methods of the invention may be used to preserve samples for other assays including mutation detection and/or hypermethylation assays. In certain embodiments, methods of the invention are used to preserve a sample for analysis using a nucleic acid integrity assay along with a mutation detection assay (e.g., a multiple mutation panel assay), a hypermethylation assay, or any combination thereof.

Nucleic acid integrity assays are known in the art and are described in, e.g., US Patent Application No. 20040043467, US Patent Application No. 20040014104, U.S. Pat. No. 6,143,529, and Boynton et al., Clin. Chem. 49:1058-65, 2003. Nucleic acid integrity assays are based on higher levels of intact nucleic acid that appear in debris from cells that lyse non-apoptotically. Healthy patient generally produces cellular debris through normal apoptotic degradation, resulting in relatively small fragments of cellular components in tissue and body fluid samples, especially luminal samples. Patients having a disease generally produce cells and cellular debris, a proportion of which has avoided normal cell cycle regulation, resulting in relatively large cellular components. As a result, the disease status of a patient is determined by analysis of patient cellular components produced in specimens obtained from the patient. The presence of such fragments is a general diagnostic screen for disease.

Nucleic acids in patient samples tend to degrade after they have been removed from the patient. This degradation can diminish the effectiveness of a nucleic acid integrity assay that scores a sample as diseased (e.g., cancerous) based on the presence of intact nucleic acids; if the sample is excessively degraded, a sample that is actually positive may appear to be negative. While not wishing to be bound by theory, it is postulated that the stabilization buffer of the invention inhibits the nucleases that degrade the nucleic acids present in the diseased patient samples.

In some aspects of the invention, the addition of a stabilization solution to a biological sample may be used to preserve nucleic acid molecules containing one or more mutations that may be detected in a multiple mutation analysis (e.g., an analysis that involves interrogating a sample for the presence of a mutation at one or more loci, for example at about 2, about 3, about 4, about 5, about 10, about 15, about 20, about 25, or more loci). In some embodiments, the addition of a stabilization solution may be used to preserve nucleic acid for a methylation specific analysis to detect the presence of hyper-methylated nucleic acid molecules at one or more loci that may be indicative of cancer, adenoma, or other disease. In some embodiments, the addition of a stabilization solution may be used to preserve nucleic acid for a combination of a nucleic acid integrity assay and/or a multiple mutation analysis and/or a methylation detection assay. Assays may be performed under conditions to detect a small amount of mutant nucleic acid in a heterogeneous sample containing an excess of non-mutant nucleic acid (e.g., where the mutant nucleic acid represents less than 10%, less than 5%, less than 1%, or about 0.1% or less of the nucleic acid at a particular locus). In some embodiments, a digital assay may be performed on the preserved nucleic acid in order to detect rare genetic events. In some aspects, stabilization methods of the invention may preserve more than 80%, 85%, 90%, 91%, 92%, 93%, 94%, 95%, 96%, 97%, 98%, 99% or more of the nucleic acids indicative of a disease (e.g., long nucleic acid fragments, nucleic acid molecules containing one or more specific mutations, and/or hyper-methylated nucleic acid molecules).

In general any body organ, tissue, or fluid known to or suspected of containing nucleic acid that can be characterized in a nucleic acid integrity analysis, multiple mutation assay, or methylation study may be used. Suitable patient samples include those likely to contain sloughed cellular debris. Such specimens include, but are not limited to, stool, blood serum or plasma, sputum, pus, colostrum, and others. In diseases, such as cancer, in which genomic instabilities or abnormalities have interfered with normal cell cycle regulation, specimens such as those identified above contain relatively intact fragments of cellular components.

The stabilization solution can be applied to a biological sample that is isolated directly from a patient, i.e., a freshly isolated biological sample. Alternatively, the method can be used on a biological sample that has been frozen (e.g., at −20° C. or −80° C.).

In aspects of the invention, stabilization solution may be added to a biological sample at any suitable ratio of sample to buffer. Ratios may be determined as a weight to volume (w/v) ratio. In some embodiments, the ratio may be about 1:1, about 1:2, about 1:3, about 1:4, about 1:5, about 1:6, about 1:7, about 1:8, about 1:9 or about 1:10 (w/v) sample to stabilization solution. However, higher or lower ratios may be used.

In aspects of the invention, the weight or volume of a biological sample may be determined before a buffer is added. According to the invention, it may be particularly important to immediately stabilize biological samples with a stabilization solution when the samples are to be interrogated for indicia of adenoma or early stage cancer. However, it also may be useful to stabilize biological samples for detecting indicia of later stage diseases or for monitoring disease progression.

In general, a stabilization solution may include one or more buffers and/or one or more chelating agents and/or one or more salts, or any combination of two or more thereof. The choices of buffer, chelating agent, and salt can be determined by the artisan. The suitability of a particular stabilization solution can be determined by comparing a nucleic acid integrity assay on samples that have been incubated with the stabilization solution to a parallel biological sample that has not been incubated with the stabilization solution. A suitable stabilization solution is a solution that shows a significant average fold increase in genome equivalents (GE) in a nucleic acid integrity assay compared to a GE determination made on parallel samples that have not been treated with the stabilization solution. Methods of calculating genome equivalents (GE) are known in the art (see, e.g., e.g., US Patent Application No. 20040043467, US Patent Application No. 20040014104, U.S. Pat. No. 6,143,529, and Boynton et al., Clin. Chem. 49:1058-65, 2003) and are illustrated in the Examples.

The temperature and pH optimum can also be determined empirically and optimized according to the combination of buffer, chelating agent and salt in the stabilization solution. While room temperature has been found to be a suitable temperature for incubating the patient sample and the stabilization solution, higher or lower temperatures (e.g., 4° C. to 16° C. or 25° C. to about 37° C.) can also be used, provided they do not undermine the effectiveness of the stabilization solution. The mixed patient sample and stabilization solution is preferably subjected to a minimum of agitation. However, according to the invention, the addition of a stabilization solution with little or no agitation is surprisingly effective at preserving nucleic acids for subsequent analysis.

In one aspect of the invention, a stabilization solution may be particularly useful when samples are not refrigerated or frozen or when there is a risk that a sample may not be maintained at a sufficiently low temperature to preserve indicia of disease. For example, a stabilization solution may be particularly useful if a sample is obtained at a remote location and mailed or delivered to a testing center. However, stabilization solutions also may be useful to preserve samples that are being processed on-site at a medical center.

Buffers

Suitable buffers may include, e.g. tris(hydroxymethyl)aminomethane, sodium phosphate, sodium acetate, MOPS, and other buffering agents as long as a buffer has the capacity to resist a 0.1 to 1 molar tris(hydroxymethyl)aminomethane or 0.1 to 1 molar phosphate ion. A combination of buffering agents can be used, so long as the solution has the required buffering capacity. Methods for determining the buffering capacity of a solution are well known in the art.

The comparison of buffering capacity is preferably carried out in the presence of the salt and chelating agent to be used in the stabilization solution, at the salt concentration to be used, and with the solutions being compared at about the same temperature, preferably at a temperature within the range of about 15° C. to about 25° C. In certain embodiments, high buffer concentrations may be used (e.g., higher than 50 mM, higher than 100 mM, higher than 200 mM, higher than 300 mM, higher than 400 mM, about 500 mM, or higher).

Chelating Agents

Chelating agents may be used in a stabilization solution. In some embodiments, chelating agents may be those that bind trace metal ions with high affinity. Non-limiting examples of chelating agents include, but are not limited to different forms of EDTA, EGTA, and other chelating agents. In certain embodiments, high chelating agent concentrations may be used (e.g., higher than 50 mM, higher than 100 mM, higher than 200 mM, higher than 300 mM, higher than 400 mM, about 500 mM, or higher). For example a stabilization solution may have an EDTA concentration of about 100 mM, about 150 mM, about 200 mM, about 250 mM, about 300 mM, or higher.

Salts

Candidate salts include, e.g., NaI, NaBr, NaCl, LiCl, KCl, KI, KBr, CsCl, GNHCl and GNSCN. In some embodiments, the salt is chaotropic and has an anion such as perchlorate, iodide, thiocyanate, acetate, trichloroacetate, hexafluorosilicate, tetrafluoroborate and the like. Cations for a chaotropic salt can include, e.g., the elements lithium, sodium, potassium, cesium, rubidium, guanidine and the like. More than one salt can be present in the buffered aqueous salt solution.

Similar stabilization methods may be used with other samples (stool, blood, plasma, serum). Any of the buffers described herein may be added as soon as the sample is obtained (e.g., as soon as a stool sample is deposited or a blood sample is drawn).

In general, the stabilization solution is added to the patient sample at a ratio of about 1 ml/gram (or ml) of patient sample to about 20 ml/gram (or ml) of patient sample. In some embodiments, the stabilization solution is provided at 1-15 ml/gram (or ml), 2-12 ml/gram (or ml), 3-11 ml/gram (or ml), or 4-7 ml/gram (or ml). However, higher or lower ratios may be used. For example, a suitable ratio of stabilization solution to patient sample may be 7 ml/gm (or ml).

In some embodiments, the patient sample and stabilization solution may be incubated at about 4 to 28° C. In some embodiments the temperature is 17 to 27° C., e.g., about 20 to 25° C. However, the sample and stabilization solution may be exposed to higher or lower temperatures (e.g., the sample and stabilization solution may be frozen). Also, a sample and buffer may be exposed to changing temperatures during transport and/or storage.

Target Genes and Loci:

Genetic Loci and Genetic Abnormalities Associated with Disease

Aspects of the invention may be used to detect the presence of a genetic abnormality in any one or more loci of interest that may be associated with a disease. For example, one or more different loci associated with an adenoma, a tumor, a cancer, a precancer or any other disease or disorder may be assayed according to methods of the invention. Examples of target nucleic acids include, but are not limited to, one or more oncogenes, tumor suppressor genes, genomic regions containing nucleic acid repeats (e.g., different forms of satellite DNA such as micro or mini satellite DNA), other genetic loci (coding or non-coding genetic loci), or combinations thereof.

In certain embodiments of the invention the presence or absence of mutations can be indicative of risk associated with developing cancer, early detection of cancer, and finally prognosis and treatment of cancer. These mutations include the following genes: MSH2, MSH6, MLH1, PMS2, BUB1, BUBR1, MRE11, CDC4, APC, beta-catenin, TGF-beta, SMAD4, p21Waf1, 14-3-3 sigma, PUMA, BAX, PRL-3, and PIK3 CA. It is appreciated that these genes are involved at different stages of the neoplastic process and therefore can be selectively used to detect or monitor tumor origination, progression or recurrence. For example, mutations in the APC/beta-catenin pathway initiate the neoplastic process. Detection of mutations in these genes is very useful for cancer risk assessment. A patient with identified mutations in the APC/beta-catenin genes is at an elevated risk for developing tumors. Most often, mutations in the APC/beta-catenin genes result in adenomas (small benign tumors). These tumor progress, becoming larger and more dangerous, as mutations in other growth-controlling pathway genes accumulate. Growth-controlling pathway genes include K-Ras, B-RAF, PIK3CA, or p53. Detection of mutations in these genes could lead to early detection of the development of tumors. If undetected and untreated (in some circumstances) the neoplastic process can be accelerated by mutations in stability genes, such as PIKSCA/PTEN, PUMA, p53/BAX, p21Waf1, 14-3-3 sigma, or PRL-3. Many of these gene products function to block cell birth, cell cycle and/or to activate cell death and apoptosis. Others like PRL-3 and PIK3CA are involved in regulating metastasis. Detection of mutations in these genes is significant for determining the clinical prognosis of a particular cancer, the treatment efficacy of a particular cancer treatment and for monitoring the progression or recurrence of a given tumor.

Adenomas

In one embodiment, aspects of the invention may be used to detect indicia of adenomas in a biological sample. According to aspects of the invention, detecting the presence of an adenoma may be useful for detecting early signs of cancer or precancer. Adenomas are typically glandular tumors or tumors of glandular origin. Adenomas may be early indicia of cancer, for example colon cancer. Not all adenomas become cancers. However, many cancers (e.g., carcinomas such as colorectal carcinomas) are thought to develop from adenomas. Indeed, a majority of colon cancers are thought to develop from adenomas. Therefore, detecting adenomas is particularly useful for identifying early signs or risks of colorectal cancer (e.g., cancerous and precancerous lesions or growths in the colon).

Adenomas may be invasive adenocarcinomas, significant adenomas, and low potential polyps. Invasive adenocarcinomas may be, for example, adenocarcinomas at different TNM stages (e.g., TNM stages 1, 2, 3, or 4). Significant adenomas may be, for example, carcinomas in-situ/high-grade dysplasias (CIS/HGD) having a diameter of greater than 1 cm, about 1 cm, less than 1 cm, or of unknown size; villous adenomas having a diameter of greater than 1 cm, about 1 cm, less than 1 cm, or of unknown size; tubulovillous adenomas having a diameter of greater than 1 cm, about 1 cm, less than 1 cm, or of unknown size, and low-grade dysplasias (LGD) with a diameter of greater than or equal to 1 cm. Low potential polyps may be, for example advanced polyps, and adenoma low-grade dysplasias (LGD) with an unknown diameter or a diameter of less than 1 cm.

According to aspects of the invention, adenomas can be detected at different positions in the colon and rectum (including the right and left colon and the transverse colon).

In one embodiment, the following panel of genetic loci may be used to detect adenomas with greater than 60% sensitivity: assays may be performed to detect one or more genetic abnormalities from a multiple mutation panel of genetic abnormalities at 22 loci including KRas mutations in codon 12 (K12p. 1, K12p. 2) and codon 13 (K13p. 2); mutations in APC codons 1309 (deletions), 1306 (mutations at position 1), 1312 (mutations at position 1), 1367 (mutations at position 1), 1378 (mutations at position 1), 1379 (mutations at position 1), 1450 (mutations at position 1), 1465 (deletions), 876 (mutations at position 1) and 1554 (insertions); mutations in p53 codons 175p. 2, 245p. 1, 245p. 2, 248p. 1, 248p. 2, 273p. 1, 273p. 2 and 282p. 1; and deletions at the BAT-26 locus. Mutations at these loci can be detected using primer extension assays (including single base extension assays and assays designed to detect micro-satellite instability such as BAT-26 deletions) or other assays that are useful to detect one or more of these genetic abnormalities.

In another embodiment, the following panel may be used to detect adenomas with greater than 60% sensitivity: assays are performed to detect hypermethylation at one or both of the HLTF and V29 loci. Hypermethylation at these loci can be detected using methylation specific primer analysis (e.g., MSP amplification) or other assays that are useful to detect hypermethylation at one or more of these genetic loci.

In one embodiment, scanning for one or more mutations at the APC-MCR may detect adenomas with greater than 74% sensitivity.

In one embodiment, the following panel may be used to detect adenomas with greater than 90% sensitivity: scanning for one or more mutations in the APC-MCR locus, exon 9 of the PIK3CA locus, exon 20 of the PIK3CA locus, B-catenin (e.g., exon 5), or a mutation in BRAF that results in a V599E amino acid change. Scanning as described herein can be used to detect one or more mutations in the APC-MCR locus, exon 9 of the PIK3CA locus, or exon 20 of the PIK3CA locus. Mutations at the BRAF locus can be detected via primer extension or other appropriate methodology.

In one embodiment, a combination of all of the above loci may be used to detect adenomas with a greater than 95% sensitivity (e.g., greater than 98% sensitivity).

Appropriate capture probes may be used to capture target nucleic acid molecules that contain one or more of the above regions of interest. Similarly, appropriate analytical or sequencing primers (e.g., primers between about 10 and about 40, or about 15 and about 30 bases long) may be used to interrogate these regions for the presence of a mutant or altered nucleotide associated with an adenoma.

Similarly, other combinations of one or more of these and/or other genomic region(s) associated with adenomas, early stage cancer or other diseases may be captured and interrogated for the presence of these or other known mutations or alterations associated with adenoma and or cancer (e.g., colorectal adenoma or cancer).

EXAMPLES

Example 1

Stool Sample Preparation

Sample Collection and Recovery of DNA from Stool

Stool samples may be frozen within 1 hour of defecation, and shipped on dry ice (−78° C.) for processing and analysis. Once received, samples may be subjected to different stabilization and/or processing techniques.

Different sample preparation methodologies used to recover DNA from stool have been previously reported (Ahlquist D A, Skoletsky J E, Boynton K A, et al. Colorectal cancer screening by detection of altered human DNA in stool: Feasibility of a multi-target assay panel. Gastroenterology 2000; 119:1219-1227; Whitney D, Skoletsky J, Moore K, et al. Enhanced Retrieval of DNA from Human Fecal Samples Results in Improved Performance of Colorectal Cancer Screening Assay. J. Mol. Diagn. 2004; 6 (4), 386-395). Stool aliquots may be weighed and combined with a stabilization buffer (e.g., 0.5M Tris, 0.15M EDTA, and 10 nM NaCl). Stabilization buffer may be added at a ratio of 7:1 volume to stool weight (mls/g). (1:7 (w/v) ratio), and the sample may be homogenized (e.g., on an Exactor (Exact Sciences)). After homogenization, a 4-g stool equivalent (~32 mls) or other amount (e.g., a 30-g equivalent) of sample may be centrifuged to remove all particulate matter. The supernatants may be treated with 20 μl TE buffer (0.01 mol/L Tris [pH 7.4] and 0.001 mol/L EDTA) containing RNase A (2.5 mg/L), and incubated at 37° C. for 1 hour. Total nucleic acid may then be precipitated (first adding $\frac{1}{10}$ volume 3 mol/L NaAc, then an equal-volume of isopropanol). Genomic DNA may be pelleted by centrifugation, the supernatant removed, and the DNA resuspended in TE. A hybrid capture technique may then be used to isolate target DNA molecules of interest.

Example 2

Blood Sample Processing (Isolation of Free DNA)

Free-DNA may be isolated from patient blood, plasma or serum preparations over a column, e.g., a Qiagen column, followed by incubation in a hybrid-capture technique to isolate specific DNA fragments.

Plasma samples may be prepared from patient blood by collecting plasma from patient and a) centrifuging the sample (e.g. 3000 rpm for 30 min); b) transferring the plasma (being careful to not transfer any of the cells) into appropriately labeled sterilized tubes and centrifuging them again (e.g. 3,000 rpm for 30 min); c) filtering the sample through a filter that excludes cells (e.g. Millipore Ultrafree-MC 0.45 micron filter Unit) followed by another spin (e.g. 3,000 rpm for 15 min); and d) discarding the top filter and transferring the samples to appropriately labeled cryovials stored at −20° C.

Serum samples may be prepared from patient blood by: a) collecting a clotted serum sample from a patient and spinning it down (e.g. 3,000 rpm for 15 min); b) loading the serum into a filter that excludes cells but not free nucleic acids (e.g. Millipore Ultrafree-MC 0.45 micron filter Unit) and centrifuging the sample (e.g. 3,000 rpm for 15 min); and c) discarding the top filter and transferring the samples to appropriately labeled cryovials stored at −20° C.

Example 3

Human DNA Purification

Target human DNA fragments may be purified from total nucleic acid preparations using a DNA affinity electrophoresis purification methodology. In brief, human DNA can be separated from the excess bacterial DNA by hybridization of the target sequences to complementary, covalently-bound oligonucleotide capture probes in acrylamide gels membranes. Crude human DNA preparations (2400 μl) may be mixed with 960 μl formamide (Sigma), 385 μl 10×TBE, and filtered through a 0.8 μm syringe filter (Nalgene, Rochester, N.Y.), then denatured (heated at 95 C for 10 min., then cooled in ice for 5 min.). The sample mix may be loaded on top of a capture membrane, and electrodes above and below the capture layer may be applied. Samples may be electrophoresed (15V, 16 h) using TBE in the reservoirs above and below the capture layer. After electrophoretic capture the remaining solution may be removed from the tubes, and the tube array may be separated from the capture plate. The capture membranes then may be washed and 40 μl of 100 mM NaOH may be added to the top of the capture membrane and incubated for 15 min. The capture plate may be placed on top of a custom molded 48-well DNA collection plate and centrifuged briefly (1900×g) to recover the eluted DNA. Then 8 μl of neutralization buffer (500 mM HCL+0.1×TE) may be added to each well of the collection plate and mixed.

In other embodiments, repetitive exposure of a nucleic acid sample (e.g., using reversed-field electrophoresis) may be used as described herein.

Quantification of Recovered Human DNA by TaqMan Analysis

TaqMan analysis may be performed on an I-Cycler (Bio-Rad) with primers against a 200-bp region of the APC gene. A probe labeled with 6-carboxyfluorescein (FAM) and 6-carboxytetramethylrhodamine (TAMRA) may be used to detect PCR product. Amplification reactions may consist of captured human stool DNA mixed with 10×PCR buffer, LATaq enzyme (Takara), 1×PCR primers (5 µM), and 1× TaqMan probe (2 µM; Biosearch Technologies). A 5 µl volume of captured DNA may be used in the PCR reactions. TaqMan reactions may be performed using standard conditions or conditions described herein or in the art.

Sequence-Specific Amplification

Polymerase chain reaction (PCR) amplifications (50 µL) may be performed on MJ Research Tetrad Cyclers (Watertown, Mass.) using 10 µL of purified DNA, 10×PCR buffer (Takara Bio Inc; Madison, Wis.), 0.2 mmol/L dNTPs (Promega, Madison, Wis.), 0.5 µmol/L sequence-specific primers (Midland Certified Reagent Co., Midland, Tex.), and 2.5 U LATaq DNA polymerase (Takara). A plurality of amplification reactions may be performed under identical thermocycler conditions: e.g., 94° C. for 5 minutes, and 40 cycles consisting of 94° C. (1 min.), 60° C. (1 min.), and 72° C. (1 min.), with a final extension of 5 minutes at 72° C. For analysis of each of the PCR products, a volume of each amplification reaction may be loaded and electrophoresed on a 4% ethidium bromide-stained NuSieve 3:1 agarose gel (FMC, Rockland, Me.) and visualized with a Stratagene EagleEye II (Stratagene, La Jolla, Calif.) still image system.

A multi-target assay designed to have 13 separate PCR reactions in the multiple mutation (MuMu) panel, and 16 PCR reactions in the DIA portion of the assay may be used. However, other multi-target assays interrogating two or more (e.g., 3, 4, 5, 6, 7, 8, 9, 10, 11, 12, 13, 14, 15, 16, 17, 18, 19, 20, 20-25, 25-30, 30-40, 40-50, or more) different target regions and or different specific mutations or types of mutation may be used according to methods described throughout the specification, including the examples.

Mutation Panel Analysis

The presence or absence of point mutations or Bat-26-associated deletions may be determined by using modified solid-phase single-base extension (SBE) reactions. Point mutation targets may include: codons K12p1, K12p2, and K13p2 on the K-ras gene; codons 876, 1306, 1309, 1312, 1367p1, 1378p1, 1379, 1450p1, 1465 and 1554 on the APC gene; and codons 175p2, 245p1, 245p2, 248p1, 248p2, 273p1, 2'73p2, and 282p1 on the p53 gene. Including the Bat-26 deletion marker, a panel may consist of 22 markers in total. For all gene targets, separate wild-type and mutant specific reactions may be performed. Details of these reactions and analysis using capillary electrophoresis have been previously described (Whitney D, Skoletsky J, Moore K, et al. Enhanced Retrieval of DNA from Human Fecal Samples Results in Improved Performance of Colorectal Cancer Screening Assay. J. Mol. Diagn. 2004; 6 (4), 386-395). Other combinations of these and/or other genetic loci and/or mutations may be interrogated.

Example 4

Electrophoretic Media

Electrophoretic media useful in the invention include any media through which charged molecules can migrate in solution in response to an electric field and to which binding partners can be immobilized, including polymeric matrices of gels, packed volumes of particles or beads, and hybrid media including beads or particles embedded in a polymeric gel matrix.

In some embodiments, one or more regions of the electrophoretic medium can be formed from different materials than the other regions (e.g., different polymeric matrices, different packed beads, hybrid gel-bead media, and combinations thereof). The materials for the different regions can be selected according to principles well known in the art to effect different separations or to selectively retain target or non-target molecules.

Polymeric Gel Media

In some embodiments, one or more of the regions of the electrophoretic medium are formed as a polymeric gel. Commonly used gel media useful in the invention include polymeric gels formed from monomers of acrylamide, agarose, starches, dextrans, and celluloses, as well as chemically modified or functionalized variants of these monomers (see, e.g., Polysciences, Inc., Polymer & Monomer catalog, 1996-1997, Warrington, Pa.), (Smithies (1959), Biochem. J 71:585; Quesada (1997), Curr. Opin. Biotech. 8:82-93).

For the separation of proteins, 5-15% (w/v) polyacrylamide gels are typically used. For small nucleic acid molecules (e.g., <1 kb), 5%-20% (w/v) polyacrylamide gels can be used. For the separation of very large nucleic acid fragments, however, the pore size of standard polyacrylamide gels can be insufficient to allow adequate movement and separation of the fragments. Therefore, lower percentage polyacrylamide gels (e.g., 2-5% (w/v)) can be used. These low percentage polyacrylamide gels, however, have poor mechanical strength. Alternatively, agarose electrophoretic media can be used for nucleic acid gels. For example, gels of 0.5-2.0% (w/v) agarose can be for most nucleic acid separations, and 0.5-1.0% (w/v) gels can be used for larger nucleic acid fragments. Low percentage agarose gels have greater mechanical strength than low percentage polyacrylamide gels.

For some methods, composite gel media containing a mixture of two or more supporting materials can be used. For example, and without limitation, composite acrylamide-agarose gels can be employed which contain from 2-5% (w/v) acrylamide and 0.5%-1.0% (wfv) agarose. In such gels, the polyacrylamide matrix performs provides the major sieving function, whereas the agarose provides mechanical strength for convenient handling without significantly altering the sieving properties of the acrylamide. In composite gels, the binding partners optionally can be attached to the component that performs the major sieving function of the gel, because that component more intimately contacts the target molecules.

In other embodiments, macroporous gels can be formed by mixing the gel-forming materials with organic liquids or pore-forming agents prior to polymerization. These liquids or pore-forming agents can be removed subsequent to polymerization to create a polymeric gel matrix with larger pores. The larger pores are useful for permitting the movement of large target molecules (e.g., genomic fragments) through the polymeric matrix material, while also maintaining the mechanical strength of the medium.

Packed Bead Media

In other embodiments, as an alternative to polymeric gel media, packed volumes of small beads or particle beds can be used as electrophoretic media. Such particle beds, which are frequently used in chromatography, have the advantage of large interstitial voids which allow for the passage of large molecules such as nucleic acid fragments>1 kb. In some embodiments, the beads have average diameters in the range of 1-5 µm, 5-50 µm, or 50-150 µm, although larger beads can also be used. Beads useful in the invention can be formed from materials including, but not limited to, agarose polymers, dextran polymers, acrylic polymers, glass, latex, polystyrene, poly(hydroxyethylcellulose), poly(ethylenoxide), a modified acrylamide, and acrylate ester.

Beads useful in the invention can be solid beads or porous beads, In some embodiments, porous beads will have diameters in the range of 10-20 µm or, more generally 10-50 µm, and can have a wide range of pore sizes. Such porous beads can include binding partners embedded within the pores and/or bound to the surfaces of the probes. Non-porous or solid beads can have a wider range of diameters, including without limitation beads in the range of 1-100 µm.

Such beads conveniently can be coated (including the interiors of pores) with one member of an affinity binding pair such that binding partners bound to the other member of the affinity binding pair can be immobilized on the beads. For example, and without limitation, beads can be coated with avidin or streptavidin and binding partners can be conjugated to biotin to cause immobilization of the binding partners on the beads. Similarly, probes can be coated with Protein A to immobilize antibody binding partners that bind to Protein A.

Beads also can be treated or coated to reduce non-specific binding or target or other molecules in a sample. For example, beads can be treated to reduce the number of hydrophobic groups (e.g., benzyl groups) on the surface, or to increase the number of hydrophilic groups (e.g., carboxyl groups) on the surface. Beads can also be coated with gelatin, bovine serum albumin or other molecules that will non-specifically bind to and "block" the surface prior to use with test samples.

In embodiments employing beads as electrophoretic media, it may be necessary to separate different regions of the electrophoretic medium by separators which are membranes or meshes that prevent the movement of the beads from one region to another in response to the electric field. Such separators must have pores sufficiently large to be permeable to the target molecules, but not permeable to the beads. Such separators can be used alone, or in combination with spacer elements or other structures between regions of the electrophoretic medium.

Hybrid Gel-Bead Media

In other embodiments, hybrid media can be formed which include small beads or particles embedded or enmeshed in a polymeric gel. Such hybrid-gel media can be formed from any of the polymeric gel materials and any of the bead materials described above. For example, and without limitation, polyacrylate or polystyrene beads can be embedded in a polyacrylamide or agarose gel matrix. In some embodiments, the binding partners will be bound to the beads prior to production of the hybrid gel-bead media. In other embodiments, however, the binding partners can be co-polymerized into the polymeric gel during its formation, or can be bound to the hybrid gel-bead media after formation.

EQUIVALENTS

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. Certain advantages and objects of the invention are not necessarily encompassed by each embodiment of the invention. Those skilled in the art will recognize, or be able to ascertain using no more than routine experimentation, many equivalents to the specific embodiments of the invention described herein. Such equivalents are intended to be encompassed by the following claims.

What is claimed is:

1. A method for monitoring disappearance, regression, progression or recurrence of diseased tissue in a patient, the method comprising the steps of:
    obtaining a first heterogeneous biological sample from the patient;
    generating a patient-specific genetic profile of diseased tissue by interrogating a plurality of genomic loci in genomic DNA and/or free DNA isolated from the first heterogeneous biological sample obtained from the patient for the presence and/or the amount of a plurality of biomarkers, wherein
        (i) the plurality of genomic loci comprises at least one mutation in each of K-ras, adenomatous polyposis coli (APC), p53, and PIK3CA, and
        (ii) the presence of at least one mutation at an individual locus is indicative of the presence of diseased tissue; and
    initiating a treatment protocol after the first heterogeneous biological sample is obtained;
    obtaining a second heterogeneous biological sample from said patient after treatment; and
    monitoring the patient-specific genetic profile by interrogating the plurality of genomic loci in genomic DNA and/or free DNA isolated from the second heterogeneous biological sample for the presence and/or the amount of the plurality of biomarkers, wherein a change of the patient-specific genetic profile is indicative of the disappearance, regression, progression or recurrence of the diseased tissue in the patient.

2. The method of claim 1, wherein the first heterogeneous biological sample is a stool, blood, plasma, serum, cerebrospinal fluid, lymph, tear, semen, urine, sweat, sputum, bronchiolar lavage, a buccal swab product, or cervical smear sample.

3. The method of claim 1, wherein the first heterogeneous biological sample is a tissue biopsy sample.

4. The method of claim 1, wherein the second heterogeneous biological sample is a stool, blood, plasma, serum, cerebrospinal fluid, lymph, tear, semen, urine, sputum, bronchiolar lavage, a buccal swab product, or cervical smear sample.

5. The method of claim 1, wherein the diseased tissue is associated with an adenoma, cancer, precancer, and/or tumor in the patient.

6. The method of claim 5, wherein the diseased tissue is associated with colon, breast, or prostate cancer.

7. The method of claim 1, wherein the treating step comprises administering of a chemotherapeutic drug.

8. The method of claim 1, wherein the treating step comprises surgery.

9. The method of claim 8, wherein the diseased tissue comprises colon cancer and the surgery is a colon resection.

10. The method of claim 1, wherein the treating step comprises radiation.

11. The method of claim 1, wherein the method comprises a step of isolating target nucleic acids containing the plurality of genomic loci from the heterogeneous biological sample using hybrid capture.

12. The method of claim 11, wherein the hybrid capture comprises reversed-field electrophoresis.

13. The method of claim 1, wherein the plurality of biomarkers comprise a plurality of tumor markers.

14. The method of claim 1, wherein the plurality of biomarkers has a sensitivity of detecting the disease of at least 80%.

15. The method of claim 1, wherein the plurality of biomarkers comprises a nucleic acid sequence substitution, deletion, and/or insertion.

16. The method of claim 1, wherein the plurality of biomarkers has a sensitivity of detecting the disease of at least 85%.

17. The method of claim 1, wherein the plurality of biomarkers has a sensitivity of detecting the disease of at least 90%.

18. The method of claim 1, wherein the plurality of biomarkers has a sensitivity of detecting the disease of at least 95%.

19. The method of claim 1, wherein the plurality of biomarkers has a sensitivity of detecting the disease of at least 97%.

20. The method of claim 1, wherein the diseased tissue is associated with a tumor selected from the group consisting of colorectal cancer, breast cancer, lung cancer, prostate cancer, bladder cancer, colorectal cancer, pancreatic cancer, gastric cancer, breast cancer, ovarian cancer, endometrial, soft tissue sarcoma, osteosarcoma, hepatocellular carcinoma, lymphoma, and leukemia.

21. The method of claim 20, wherein the tumor is a colorectal tumor.

22. The method of claim 1, wherein the one or more mutations comprise at least 5 mutations.

23. The method of claim 1, wherein the one or more mutations comprise at least 10 mutations.

24. The method of claim 1, wherein the one or more mutations comprise at least 15 mutations.

25. The method of claim 1, wherein the first and second biological samples are different types of samples.

26. The method of claim 1, wherein said first and/or second biological sample is serum or plasma.

27. The method of claim 1, wherein said interrogating comprises allele-specific PCR.

28. The method of claim 1, wherein said interrogating comprises mismatch amplification mutation analysis.

29. The method of claim 1, where in the plurality of genomic loci comprises at least 10 different loci.

30. The method of claim 29, wherein the plurality of genomic loci comprises at least 15 different loci.

31. The method of claim 30, wherein the plurality of genomic loci comprises at least 20 different loci.

32. The method of claim 31, wherein the plurality of genomic loci comprises at least 25 different loci.

33. The method of claim 1, further comprising a step of recommending a therapeutic decision based on the change in the patient specific genetic profile.

34. The method of claim 1, wherein the method further comprises evaluating if the treating step is effective for the disease based on the change in the patient specific genetic profile.

35. The method of claim 1, wherein said interrogating comprises digital assay analysis.

36. The method of claim 1, wherein said interrogating comprises high complexity sequence analysis.

37. The method of claim 1, wherein said interrogating comprises a quantification of the plurality of biomarkers.

38. A method for monitoring disappearance, regression, progression or recurrence of diseased tissue in a patient, the method comprising the steps of:
   generating a patient-specific genetic profile of diseased tissue by interrogating a plurality of genomic loci in genomic DNA and/or free DNA isolated from a biological sample obtained from the patient for the presence and/or the amount of a plurality of biomarkers, wherein
      (i) the plurality of genomic loci comprises at least one mutation in each of K-ras, adenomatous polyposis coli (APC), p53, and PIK3CA, and
      (ii) the presence of at least one mutation at an individual locus is indicative of the presence of diseased tissue; and
   monitoring the patient-specific genetic profile by interrogating the plurality of genomic loci in genomic DNA and/or free DNA isolated from a second heterogeneous biological sample for the presence and/or the amount of the plurality of biomarkers, wherein a change of the patient-specific genetic profile is indicative of the disappearance, regression, progression or recurrence of the diseased tissue in the patient.

39. The method of claim 38, wherein said first and/or second heterogeneous biological sample is serum or plasma.

* * * * *